US010042976B2

(12) United States Patent
Colwell et al.

(10) Patent No.: US 10,042,976 B2
(45) Date of Patent: *Aug. 7, 2018

(54) DIRECT IDENTIFICATION AND MEASUREMENT OF RELATIVE POPULATIONS OF MICROORGANISMS WITH DIRECT DNA SEQUENCING AND PROBABILISTIC METHODS

(71) Applicant: CosmosID Inc., College Park, MD (US)

(72) Inventors: Rita R. Colwell, Bethesda, MD (US); Boyd Thomas Livingston, Columbia, MD (US); David Jakupciak, Bethesda, MD (US); Nur A. Hasan, College Park, MD (US); John P. Jakupciak, Boonsboro, MD (US); Douglas M. Brenner, Colleyville, TX (US)

(73) Assignee: CosmosID Inc., Rockville, MD (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/934,029

(22) Filed: Jul. 2, 2013

(65) Prior Publication Data

US 2014/0136120 A1    May 15, 2014

Related U.S. Application Data

(63) Continuation of application No. 13/014,112, filed on Jan. 26, 2011, now Pat. No. 8,478,544, which is a continuation-in-part of application No. 12/276,037, filed on Nov. 21, 2008, now Pat. No. 8,775,092.

(60) Provisional application No. 60/989,641, filed on Nov. 21, 2007.

(51) Int. Cl.
*G06F 19/24* (2011.01)
*G06F 19/22* (2011.01)
*G06F 19/28* (2011.01)
*G06F 19/10* (2011.01)

(52) U.S. Cl.
CPC .............. *G06F 19/24* (2013.01); *G06F 19/22* (2013.01); *G06F 19/28* (2013.01)

(58) Field of Classification Search
None
See application file for complete search history.

(56) References Cited

U.S. PATENT DOCUMENTS

| | | | |
|---|---|---|---|
| 4,923,978 A | 5/1990 | McCormick | |
| 5,057,426 A | 10/1991 | Henco et al. | |
| 5,218,099 A | 6/1993 | Reyes et al. | |
| 5,733,729 A | 3/1998 | Lipshutz et al. | |
| 5,871,697 A | 2/1999 | Rothberg et al. | |
| 5,982,932 A | 11/1999 | Prokoski | |
| 7,602,785 B2 | 10/2009 | Dharmapurikar et al. | |
| 7,680,790 B2 | 3/2010 | Indeck et al. | |
| 7,702,683 B1 | 4/2010 | Kirshenbaum | |
| 7,870,385 B2 | 1/2011 | Risan et al. | |
| 2002/0120408 A1 | 8/2002 | Kreiswirth et al. | |
| 2003/0044771 A1 | 3/2003 | Anderson et al. | |
| 2003/0233197 A1 | 12/2003 | Padilla et al. | |
| 2004/0219580 A1 | 11/2004 | Dunn et al. | |
| 2005/0086520 A1 | 4/2005 | Dharmapurikar et al. | |
| 2005/0149272 A1 | 7/2005 | Pe'Er et al. | |
| 2005/0255459 A1 | 11/2005 | Fofanov et al. | |
| 2006/0259249 A1 | 11/2006 | Sampath et al. | |
| 2007/0067108 A1 | 3/2007 | Buhler et al. | |
| 2007/0260602 A1 | 11/2007 | Taylor | |
| 2007/0263163 A1 | 11/2007 | Mun et al. | |
| 2009/0150084 A1 | 6/2009 | Colwell et al. | |
| 2009/0270277 A1 | 10/2009 | Glick et al. | |
| 2009/0319506 A1 | 12/2009 | Ngan | |
| 2010/0049445 A1 | 2/2010 | Fofanov et al. | |

FOREIGN PATENT DOCUMENTS

| | | |
|---|---|---|
| EP | 0515484 B1 | 4/1995 |
| EP | 0512767 A1 | 7/1996 |
| WO | WO 95/13368 | 5/1995 |
| WO | WO 96/18731 | 6/1996 |
| WO | WO 97/10331 | 3/1997 |

(Continued)

OTHER PUBLICATIONS

European Office Action dated May 19, 2015 for Appln. No. 08 867 952.7-1405.
Buhler et al., "Mercury Blastin: Faster DNA Sequence Comparison Using a Streaming Hardware Architecture," Proc. of Reconfigurable Systems Summer Institute, Jul. 2007 (11 pages).
Kent, "BLAT—The BLAST-Like Alignment Tool," Genome Res., vol. 12, pp. 656-664 (2002).
Ning et al., SSAHA: Fast Search Method for Large DNA Databases, Genome Res., vol. 11, pp. 1725-1729 (2001).
Rosen et al., "Signal Processing for Metagenomics: Extracting Information from the Soup," Current Genomics, vol. 10, pp. 493-510 (2009).

(Continued)

*Primary Examiner* — Lori A. Clow
(74) *Attorney, Agent, or Firm* — Sheppard Mullin Richter & Hampton LLP

(57) ABSTRACT

The present invention relates to systems and methods capable of characterizing populations of organisms within a sample. The characterization may utilize probabilistic matching of short strings of sequencing information to identify genomes from a reference genomic database to which the short strings belong. The characterization may include identification of the microbial community of the sample to the species and/or sub-species and/or strain level with their relative concentrations or abundance. In addition, the system and methods may enable rapid identification of organisms including both pathogens and commensals in clinical samples, and the identification may be achieved by a comparison of many (e.g., hundreds to millions) metagenomic fragments, which have been captured from a sample and sequenced, to many (e.g., millions or billions) of archived sequence information of genomes (i.e., reference genomic databases).

14 Claims, 23 Drawing Sheets

(56) References Cited

FOREIGN PATENT DOCUMENTS

WO  2004/007763 A2  1/2004
WO  2006/096324 A2  9/2006

OTHER PUBLICATIONS

Rumble et al., :SHRiMP: Accurate Mapping of Short Color-space Reads, PLos Comput Biol, vol. 5, issue 5, e1000386, 11 pages (2009).
Stranneheim et al., "Classification of DNA Sequences Using Bloom Filters," Bioinformatics, vol. 26, No. 13, pp. 1595-1600 (2010).
Zhu et al., "Bayesian Adaptive Sequence Alignment Algorithms," Bioinformatics, vol. 14, No. 1, pp. 25-39 (1998).
J. P. Jakupciak, et al., "Barcoding Methodology and Applications—Biological agent detection technologies," Molecular Ecology Resources, vol. 9, Suppl. 1, pp. 51-57 (May 2009).
Rannala et al. (Journal of Mol. Evol. (1996) vol. 43, pp. 304-311).
Sagot et al. (Theoretical Computer Science (1997) vol. 180, pp. 115-137).
Ludwig et al. (Nucleic Acids Research (2004) vol. 32, pp. 1363-1371).
Huson et al. Genome Research (2007) vol. 17, pp. 377-386; first published online on Jan. 25, 2007.
Pavesi et al. (Bioinformatics (2001) vol. 17, Suppl. 1, pp. S207-S214).
Cowan et al. (Trends in Biotechnology (2005) vol. 23, No. 6, pp. 321-329).
Tringe et al. (Science (2005) vol. 308, pp. 554-557).
Ivnitski et al. (Biotechniques (2003) vol. 35, pp. 862-869).
Extended European Search Report dated Mar. 8, 2016 for Appln. No. 12739779.2.
Indian Office Action dated Dec. 15, 2016 for Appln. No. 221/KOLNP/2010.
Zhu et al., "Bayesian adaptive sequence alignment algorithms", Bioinformatics, vol. 14, No. 1, 1998, pp. 25-39.
U.S. Office Action dated Sep. 23, 2016 for Appln. No. 14/291,930.
Final Office Action U.S. Appl. No. 14/291,930 dated Jun. 26, 2017.

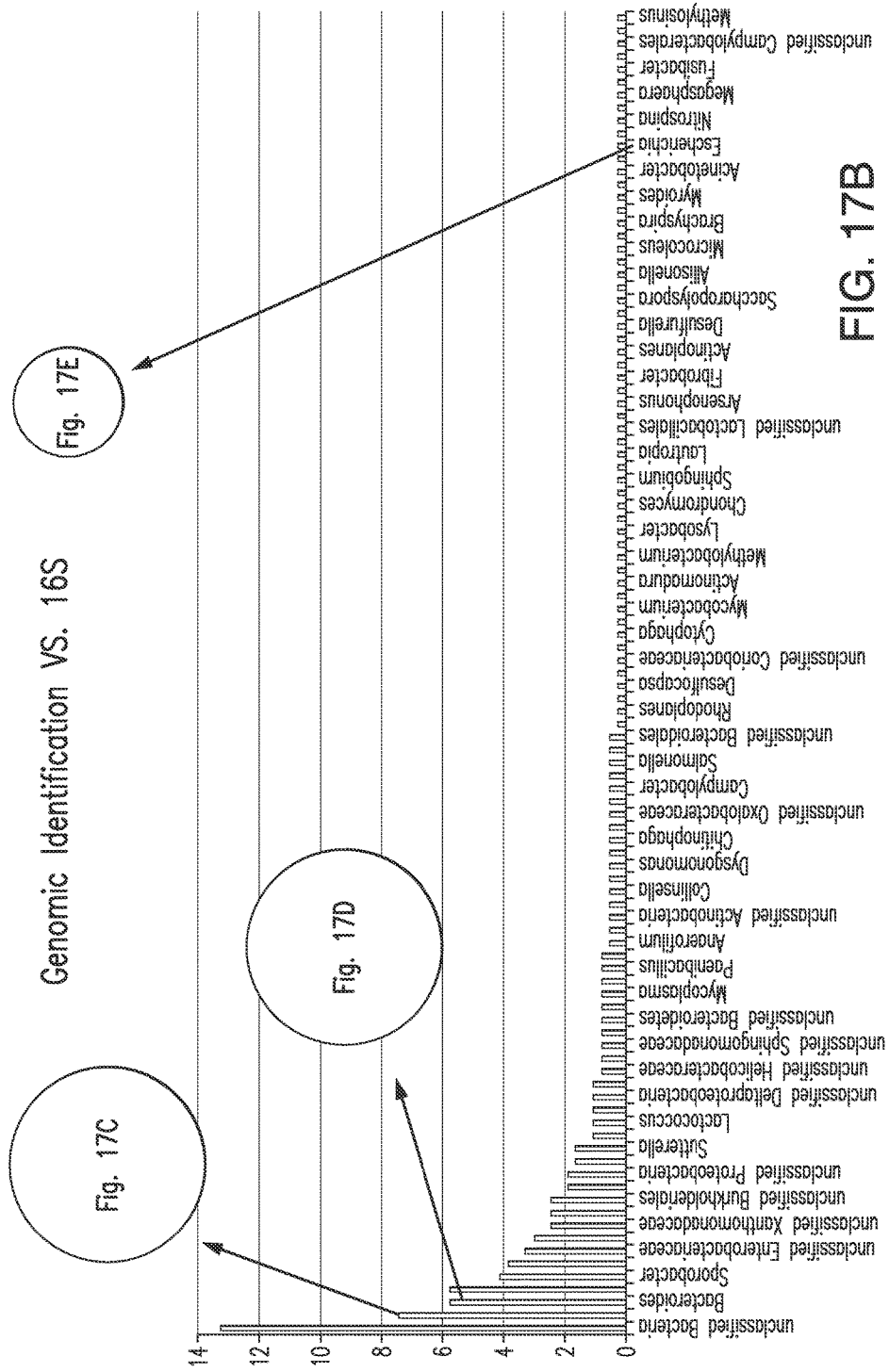

DIRECT IDENTIFICATION AND MEASUREMENT OF RELATIVE POPULATIONS OF MICROORGANISMS WITH DIRECT DNA SEQUENCING AND PROBABILISTIC METHODS

CROSS-REFERENCE TO RELATED APPLICATIONS

The present application is a continuation of U.S. patent application Ser. No. 13/014,112, filed Jan. 26, 2011, which is a continuation-in-part of U.S. patent application Ser. No. 12/276,037, filed Nov. 21, 2008, which claimed the benefit of priority to U.S. Provisional Application Ser. No. 60/989,641, filed on Nov. 21, 2007, the entire disclosures of which are incorporated herein by reference.

BACKGROUND

Field of Invention

This invention relates to a system and methods for the characterization of organisms and more particularly, to the characterization of the identities and relative populations of organisms in a sample. The characterization may be specific to the species and/or sub-species and/or strain level and may rely on probabilistic methods that compare sequencing information from metagenomic fragment reads to sequencing information of one or more genomic databases.

Discussion of the Background

Current nucleic acid methods for identifying populations of organisms are specific only to the genus level (16S rDNA) for bacteria, viruses, and other microbial organisms and do not identify the populations down to the species, sub-species and strains of organisms within the sample. Current techniques for detecting and identifying one or a small number of bacteria to the genus, species and/or sub-species level rely on static methods, such as polymerase chain reaction (PCR) and microchip arrays, to detect signatures of a pre-specified organism or plurality of pre-specified organisms. Current methods for detecting and identifying viruses require specific nucleic acid tests and do not produce data on population diversity. Complete sequencing of virus genomes has been used to demonstrate virus diversity. Conventional methods generally employ laboratory culturing methods for bacteria, fungi and parasites and are time consuming and expensive.

In none of these cases are relative populations able to be precisely determined nor are any of these methods able to detect and identify simultaneously the organisms present in microbial populations with respect to the specific taxa (genus, species, sub-species, and strain) of bacteria, viruses, parasites, fungi, or nucleic acid fragments including plasmids and mobile genomic components. In addition, given the rapid rate of genomic mutation, and growing evidence of horizontal gene transfer, static methods that rely on predetermined signatures produce false negative results if (a) mutation has occurred in the nucleic acid sequence of the sample relative to the signature, (b) the target signature was horizontally transferred, or (c) genomic near neighbors are present in the sample.

In the diagnosis of infectious disease, conventional microbiology still relies on time consuming and laborious culturing methods and cumbersome tests for bacteria, viruses, parasites, and fungi, and also on immunological and molecular nucleic acid tests. Additional nucleic acid assays are generally used to determine the presence of specific bacteria, viruses or uncultivable bacteria. In a significant fraction of samples and up to 25% of all samples, no identifiable causative agent specific to the symptoms of the patient is identified. Moreover, it is generally assumed that an infectious disease is always caused by a single microbial agent or plurality of the agent, collectively inducing the observed symptoms, when more than one or a few cells of the agent are present.

Background bacterial populations or microbiomes (bacteria), mycobiomes (fungi) and viromes (viruses), at the species and strain levels cannot be rapidly or easily determined (i.e., within hours and with a single method or less) by current methods. However, determining the cause of disease may require normalizing results to background populations, but current methods lack the ability to do this. In food science, such relative comparisons to microbial background, down to the sub-species and/or strain level, are required to determine the source of food contamination and degree of pathogenicity.

For example, benign strains of *Escherichia coli* are abundant in nature, but such strains can mutate, acquire genes encoding for pathogenesic properties and/or toxin production and become toxigenic (e.g., *E. coli* O157:H7). Recently, six (6) new pathogenic strains of *E. coli* non-O157 (O111, O121, O26, O45, 0103 and O145) have been identified. These new pathogenic strains of *E. coli* are much less known than *E. coli* O157 but are just as capable of causing serious illness, including kidney failure, which is usually fatal. These new pathogenic strains of *E. coli* are much harder to identify in a microbiome using conventional methods because, although these new strains have been identified from their whole DNA genomes, tests using conventional static methods technology and involving a genetic signature have not been developed.

Given the frequency and propensity of genetic mutation in nature, it is probable that additional pathogenic strains of *E. coli* and other bacteria will continue to develop and evolve and, therefore, cause disease. Such continuing genetic mutation, a naturally occurring phenomenon, requires a universal method to facilitate identification even when mutation has occurred. Accordingly, there is a need in the art both for a universal method capable of microbial identification at the species and strain levels and for a method that accounts for biodiversity and mutation. Since DNA and RNA base pairs characterize all living organisms, including microorganisms and nucleic acid fragments like plasmids, and direct DNA sequencing is the standard for DNA base-pair identification, there is a need in the art for universal genomic identification at the sub-species and strain level using direct DNA and RNA sequencing of metagenomic samples.

Moreover, monitoring populations of microorganisms in the environment (e.g., in the water supply) and tracing them to infectious disease in patients (e.g., cholera) requires specificity of identification to the sub-species and/or strain level to diagnose the disease and its source. In addition, analysis of microbiomes in nature is required to understand antibiotic resistance and to monitor and prevent epidemic outbreaks or pandemics. Since microorganims are ubiquitous and many, if not most, exist both in environmentally friendly (non toxigenic commensal) forms and also in forms that are a biothreat to humans (highly toxigenic and/or invasive pathogen), they cannot be completely eradicated; the only way to minimize or prevent infection is to minimize exposure to pathogenic forms of microbes when their concentrations are high, and to identify and track specific pathogenic species and strains infecting patients.

Basic Local Alignment Search Tool (BLAST) analysis has become a ubiquitous method of interrogating sequence data. Many data-search methods have been developed that are based on improvements to BLAST. These include systems and methods for generating indexes and fast searching of "approximate", "fuzzy", or "homologous" (perfect-matching) matches for a large quantity of data. The data are indexed to generate a search tree taxonomy. Once the index is generated, a query can be provided to report hits within a certain neighborhood of the query. In BLAST, a local distance of a local sequence space is used to generate local search tree branches.

However, there are limitations to using BLAST output E-values, which describe the number of hits one can expect to see by chance when searching a database of a particular size and are used to gauge the significance of a match, as criteria for data parsing. While this measurement is possible, the output is often skewed by both the database used for comparison and the length of the match. Small regions of high similarity can generate an artificially low E-value and negate the global level of similarity exhibited by the sequence. The value of the BLAST score varies with the length of the nucleotide queried, and hence is not suitable alone for comparative analysis using universal cutoffs.

Previously, direct application of sequencing for rapid, multiplex diagnostics had not been possible. Direct analysis of samples was considered too complex to interpret and selective methods (e.g., culture) are employed to minimize the number of organisms (mostly to one type) for analysis. The capability to detect all pathogens using a single platform has not been possible. Biodefense, Force Protection, agriculture and global health will benefit from sequence-based identification of all pathogens in a sample and pathogen profiling for medical decision-making.

Pathogen identification techniques that do not necessarily rely on conventional culture methods include immunological techniques, whereby molecules unique to the pathogen (generally proteins) are detected using antibodies that specifically bind to the unique molecules, and a variety of techniques that target specific DNA or RNA sequences, collectively know as nucleic acid techniques (NAT) or molecular diagnostic techniques. Current immunological and NAT methods are useful for recognizing a limited range of pathogens under highly specific conditions, but each of these methods is subject to inadequacies.

Immunological techniques, or immunoassays, are known to suffer several critical weaknesses that limit their effectiveness in medical diagnosis. These include the volume and specificity of the reagents, cross-reactivity, and poor immunogenicity of some organisms, among the shortcomings. For example, often it is difficult to produce antibodies that will react specifically with the target pathogen without reacting to other pathogens (i.e., cross-reactivity). There are many pathogens that vary the molecules on their surfaces (e.g., *Niesseria gonorrheae*), making it impossible to detect all members of a given target group. Many immunoassay formats, such as rapid agglutination tests for Type A Strep, require large numbers of organisms for detection. This makes early detection of infections difficult or requires culture of the microorganisms prior to immunological detection.

Nucleic acid methods are much more specific than immunological methods because they target genetic material of the pathogen. Almost all NAT methods require amplification of the target nucleic acid by the Polymerase Chain Reaction (PCR). Limitations of PCR include: (a) the library of DNA primers to recognize sequences on pathogen genomes is limited; (b) mutants, strains, and engineered pathogens are not always readily detected if at all; (c) because of the limited DNA primer libraries, there is little or no recognition redundancy to exclude false positive or negative reactions; (d) primer/signature erosion occurs; and (e) unknown pathogens cannot be recognized because recognition of any pathogen requires previous knowledge of the nucleotide sequence of the particular pathogen's genetic material.

Sequencing-based methods have been used for whole genome analysis, but not for characterizing and identifying populations of microorganisms or as a predictive and forensic tool for decision making. For example, methods for identifying species and subspecies in a biological sample through selective amplification of segments of nucleic acid have been developed. Such methods use a primer or code for a specific target region (usually a gene, genes, or fragments of genes, including mitochondrial DNA) present in a minute fraction of all the populations in a sample. The methods involve DNA extraction from a sample, amplification of divergent segments of the target by PCR or an equivalent technique, using primers of regions with high evolutionary conservation between species and subspecies, analysis of the amplified segment by comparison of its size in base pairs with a pre-established standard of sizes and/or analysis of the amplified segment by DNA sequence comparison of the resulting sequence with a subset of specific sequences of fractions of a group of species or subspecies queried on a computer database.

These methods have been used for genetic analysis of a biological species employing a sample (biological material) derived from single isolates or from samples containing dual or heterogeneous mixtures. Amplification of a region of DNA of the sample, corresponding to a pre-determined and narrow genome position(s), is done to determine the size in base-pairs and/or the precise DNA sequence followed by mapping that region via taxonomic identification. The mapping is done against a reference database of organisms of amplified regions containing pre-established sizes and/or DNA sequences of the corresponding region of a plurality of species and/or subspecies.

All of these methods have limited use when a sample comprises a mixture of organisms. They can only confirm the presence of a pre-known or suspected organism, but they cannot identify each of the organisms present in the sample and cannot identify to the species, sub-species, and/or strain level. In addition, if a pre-known organism were present, but had undergone mutation in the pre-specified sequence, such methods would indicate a false negative. The natural processes of mutation, genetic deletions and alterations or engineered mutations are all part the creation of biodiversity which cannot be detected or even addressed with existing prior art methods.

Therefore, a mechanism is needed to identify simultaneously a plurality of organisms in a given sample with a single test without having to use multiple probes and without prior knowledge of organisms present in the sample. It also desirable to distinguish very similar or interrelated species, sub-species and strains for medical, agricultural, and industrial applications.

There are many life-threatening circumstances in which it would be useful to analyze and sequence the DNA and/or RNA in a sample, for example, in response to an act of bioterrorism where a fatal pathogenic agent had been released into the environment. In the past, such results have required involvement of many people, which demand too much time. As a result, rapidity and accuracy may suffer.

A bioterrorist attack or an emerging epidemic, requires first responders, i.e. physicians in the emergency room (their options or bed-side treatments), to make immediate decisions for treatment, and food manufacturers, distributors, retailers, and public health personnel throughout the country to identify rapidly, accurately, and reliably the pathogenic agents and disease(s) they cause. Pathogenic agents can be transmitted in food, air, soil, water, and animal, plant and human tissue and by clinical presentation in emergency rooms. Because the agent(s) and/or potential disease(s) can be immediately life-threatening and/or highly contagious, identification must be both rapid and accurate. If this is not possible, it represents a significant weakness in infectious disease control, homeland security, and bioterrorism response.

A method and system are needed to identify rapidly and accurately more than a single organism (multiplexing) in a sample and indicate if a species, strain and/or substrain are present employing genome comparison of nucleic acids present in the sample to nucleic acids present in a reference genomic database.

Rapid advances in biological engineering have dramatically impacted the design and capabilities of DNA sequencing tools, including high through-put sequencing, a method of determining the order of bases in DNA, and mapping the genetic variation that reveals the genetic underpinning of human disease. This approach is useful when sequencing many different DNA templates with any number of primers. Despite these important advances in biological engineering, little progress has been made in building devices to quickly identify sequence information and transfer data more efficiently and effectively.

Traditionally, DNA sequencing was accomplished by a dideoxy method, commonly referred to as the Sanger method [Sanger et al, 1977], that used chain terminating inhibitors to stop the extension of the DNA chain during DNA synthesis.

Methods for sequencing strategies continue to be developed. For example, it is possible to build an array of DNA sequences (microarrays) and hybridize complementary sequences in a process commonly referred to as sequencing-by-hybridization. Another technique considered state-of-the-art employs primer extension, followed by cyclic addition of a single nucleotide, with each cycle followed by detection of the incorporation event. The technique referred to as sequencing-by-synthesis or pyrosequencing, including fluorescent in situ sequencing (FISSEQ), is reiterative in practice and involves a serial process of repeated cycles of primer extension while the target nucleotide sequence is sequenced. These sequencing methods cannot rapidly identify an organism from the data of an isolate, and no tools currently exist for identifying a mixture of organisms based on metagenomic data created by these sequencing methods. Moreover, conventional methods and systems for identifying organisms in metagenomic samples based on nucleotide data generated by sequencers do not exist.

Despite these advances, there is a need for rapid genome identification methods and systems, including multidirectional electronic communication of nucleic acid sequence data, clinical data, therapeutic intervention, and tailored delivery of therapeutics to targeted populations to streamline responses and speed diagnosis of infectious disease, conserve valuable medical supplies, and contain bioterrorism, inadvertent release, and emerging pathogenic epidemics. In addition, a mechanism is needed to identify simultaneously a plurality of organisms in a given sample with a single test without having to use multiple probes, and it is desirable to distinguish very similar or interrelated species, sub-species and strains for medical, agricultural, and industrial applications.

SUMMARY

The present invention relates to systems and methods capable of characterizing populations of microorganisms within a sample. In some embodiments, the characterization utilizes probabilistic matching to identify microbial genomes to which metagenomic fragments extracted from the sample are related. The characterization may further include identification of the microbial community of the sample to the species and/or sub-species and/or strain level with their relative concentrations or abundance. In addition, the systems and methods may enable rapid identification of organisms, including both pathogens and commensals in clinical, food, water and environmental samples, and the identification may be achieved by comparison of many (e.g., hundreds to millions) metagenomic fragments, which have been captured from a sample and sequenced, to many (e.g., millions or billions) of archived sequence information of genomes (i.e., reference genomic databases). Achieving accurate metagenomic characterization at the high ends of these spectra, that is, comparing tens of millions of metagenomic fragments to archived genomic databases comprising billions of nucleotides, is previously undocumented in the literature.

In one aspect, the present invention provides a method of characterizing biological material in a sample containing genetic material from a plurality of organisms. The method comprises performing probabilistic methods that compare a plurality of metagenomic fragment reads obtained from the sample with a plurality of genome reads from a reference database containing genomic identities of organisms and produce probabilistic results. The method also comprises determining the identities of organisms contained in the sample at least to the species level using the probabilistic results. The method steps are performed using a processor and memory.

The method may comprise determining the identities of organisms contained in the sample at least to the sub-species level using the probabilistic results. The method may also comprise determining the identities of organisms contained in the sample at the strain level using the probabilistic results. The method may further comprise characterizing the relative populations of species and/or sub-species and/or strains of the identified organisms.

The method may comprise characterizing the relative populations of the identified organisms by correlating probabilities of the probabilistic results to relative populations at the species and/or sub-species and/or strain levels.

In one embodiment of the invention, the probabilistic results may be in the form of a probability map of probabilities that species and/or sub-species and/or strains of organisms contained within the reference database are present within the sample. The probability map may enable correlation of the probabilities of the probability map with relative populations and/or concentrations of organisms contained within the sample. The method may further comprise compensating for machine error by using a number of statistically significant metagenomic fragment reads large enough that machine errors are normalized. The machine error for which the normalization compensates may comprise machine error of a sequencer used to generate the plurality of metagenomic fragment reads, and the compensating may comprise using enough metagenomic fragment reads that machine error of the sequencer is normalized to a near-zero value.

The method may further comprise generating the plurality of metagenomic fragment reads. The generating the plurality of metagenomic fragment reads may comprise sequencing metagenomic fragments extracted from the sample. The method may further comprise extracting the metagenomic fragments from the sample.

In yet another embodiment of the invention, the method comprises accounting for biodiversity. The accounting for biodiversity may comprise identifying: (a) mobile genetic elements through lateral gene transfer, recombination, or plasmid or other mobilome insertion; (b) insertions and deletions; and (c) identification and detection of near relation (e.g., cousin) strains related by mutation, insertion, and/or deletion.

In an embodiment of the invention, the reference database contains the genomic identities of one or more of the plurality of organisms contained in the sample. Each of the plurality of metagenomic fragment reads may have a read length greater than or equal to 12 base pairs and less than or equal to 100 base pairs. However, metagenomic fragment reads having a length longer than 100 base pairs may additionally, or alternatively, be used. The probabilistic methods comprise, for each of the plurality of metagenomic fragment reads, detecting and retaining causal correlations between the metagenomic fragment read and genome reads from the reference database containing genomic identities of organisms; and integrating the retained causal correlations by genomic strain and species to identify a set of genomes of microorganisms contained in the sample. The probabilistic methods may further comprise creating independent pattern sets of subset inclusion and subset exclusion from the set of genomes, and, for each independent pattern set, pairing the set against target reads. Each of the pairings may result in an independent estimate of concentration of the genome in the set. The independent estimates may give a fine-grain estimate of genomic strain concentrations even for closely related microbial communities.

In another embodiment of the invention, the probabilistic methods comprise probabilistic matching. The probabilistic methods may comprise: primary filtering to determine what species and strains from the reference database can be in the metagenomic sample; and secondary and tertiary filtering to eliminate both false negatives and false positives and to identify at strain level what organisms are contained in the sample.

In one embodiment of the invention, the identified organisms include genomes of bacteria, viruses, parasites, fungi and/or nucleic acid fragments including plasmids and mobile genomic components. The identifying organisms contained within the sample may be capable of identifying bacteria, viruses, parasites, fungi, and nucleic acid fragments including plasmids and mobile genomic components contained within the sample. The plurality of metagenomic fragment reads may be sequence reads of metagenomic fragments extracted from the sample. The metagenomic fragments extracted from the sample are from genomic nucleic acid, protein and/or a combination with metabolites extracted from the sample. Each of the metagenomic fragments extracted from the sample may be a fragment of a nucleic acid sequence. Each of the metagenomic fragments extracted from the sample may be a fragment of a deoxyribonucleic acid (DNA) sequence. Each of the metagenomic fragments extracted from the sample may be a ribonucleic acid (RNA) sequence. Each of the metagenomic fragments extracted from the sample is a fragment of a plasmid or other unit nucleic acid sequence.

In yet another embodiment of the invention, the plurality of metagenomic fragment reads are obtained from the sample by: collecting the sample, extracting metagenomic fragments from the sample, and sequencing the metagenomic fragments.

In another embodiment of the invention, the plurality of metagenomic fragment reads that may be obtained from the sample are included in a metagenomic file. The method may further comprise creating a list of reference words for each of the plurality of genome reads from the reference database containing genomic identities of organisms, and creating a catalog of lists of reference words. The method may further comprise creating a list of reference words for each of the plurality of genome reads from the reference database containing genomic identities of organisms, and creating a catalog of lists of reference words. Each list of reference words may be associated with one or more categories. Each of the one or more categories may be associated with a genus, species or strain. The method may further comprise creating a list of sample sequence words for each of the plurality of metagenomic fragment reads obtained from the sample. The comparison of the plurality of metagenomic fragment reads obtained from the sample with the plurality of genome reads from the reference database containing genomic identities of organisms may comprise: for each of the sample sequence words of the list of sample sequence words, comparing the sample sequence word to the reference words of each of the lists of reference words, and identifying matches between the sample sequence word and one or more of the reference words. The identified matches may be exact matches. The identified matches may comprise inexact matches. The method may further comprise: for each of the plurality of genome reads from the reference database, summing the number of matches for the genome read, and comparing the sum of the number of matches for each of the plurality of genome reads to the sums of the numbers of matches for each of the other of the plurality of genome reads. The method may further comprise: for each of the plurality of genome reads from the reference database, summing the number of unique matches for the genome read, and comparing the sum of the number of unique matches for each of the plurality of genome reads to the sums of the numbers of unique matches for each of the other of the plurality of genome reads. A unique match may be a match of a sample sequence word to a reference word contained in only one of the lists of reference words. The creating the list of reference words comprises splitting a genome read from the reference database into words at a word boundary character. The creating the list of reference words may comprise saving only words having a length greater than or equal to a minimum word length. The minimum word length may be equal to nineteen letters. The method may further comprise populating a hash table with the reference words of each of the created lists of reference words.

In another aspect, the present invention provides an apparatus for characterizing biological material in a sample containing genetic material from a plurality of organisms. The apparatus comprises a processor and memory, wherein the processor and memory are configured to: perform probabilistic methods that compare a plurality of metagenomic fragment reads obtained from the sample with a plurality of genome reads from a reference database containing genomic identities of organisms and produce probabilistic results, and determine the identities of organisms contained in the sample at least to the species level using the probabilistic results. The processor and memory may also be configured to determine the identities of organisms contained in the sample at least to the strain level using the probabilistic results.

In yet another aspect, the present invention provides a computer-readable medium containing instructions that, when executed by a computer, cause the computer to execute the steps of: performing probabilistic methods that compare a plurality of metagenomic fragment reads obtained from a sample containing genetic material from a plurality of organisms with a plurality of genome reads from a reference database containing genomic identities of organisms and produce probabilistic results; and determining the identities of organisms contained in the sample at least to the species level using the probabilistic results. The instructions may also cause the computer to execute the step of determining the identities of organisms contained in the sample at least to the strain level using the probabilistic results.

In still another aspect, the present invention provides a method of characterizing biological material in a sample. The method comprises: receiving sequencing information about said biological material in said sample, and identifying a plurality of species of organisms present in said biological material in said sample via probabilistic methods. The method steps are performed using a processor and memory. The sequencing information may comprise a plurality of sequences of nucleotide fragments from nucleic acid molecules extracted from said biological material in said sample, and the identifying may comprise comparing said plurality of sequences of nucleotide fragments to nucleic acid sequences in a database. The probabilistic methods may include one or more of perfect matching, subsequence uniqueness, pattern matching, multiple subsequence matching within n length, inexact matching, seed and extend, distance measurements and phylogenetic tree mapping. The identifying may comprise detecting variations between strains, mutants and engineered organisms and characterizing unknown organisms and polymorphisms. The method may comprise: extracting nucleotide fragments from nucleic acid molecules from said biological material in said sample; and generating a plurality of sequences of nucleotide fragments from nucleic acid molecules extracted from said biological material in said sample, wherein said sequencing information comprises said plurality of sequences of nucleotide fragments.

Another aspect of the present invention is a method of identifying a biological material at the species and strain level in a sample, comprising: obtaining a sample comprising the biological material, extracting one or more nucleic acid molecule(s) from the sample, generating sequence information from the nucleic acid molecule(s) and probabilistic-based comparing the sequence information to nucleic acid sequences in a database. Identifying a biological material includes, but not limited to, detecting and/or determining the genomes present in the sample, nucleic acid sequence information contained within the sample, ability to determine the species of the a biological material, ability to detect variations between strains, mutants and engineered organisms and characterizing unknown organisms and polymorphisms. Biological material includes, but not limited to, DNA, RNA and relevant genetic information of organisms or pathogens associated with bacteria, viruses, fungi, parasites, plasmids and other nucleic acid fragments.

In one embodiment of the invention, the nucleotide fragment is compared to the nucleic acid sequences in a database via probabilistic matching, including, but not limited to Bayesian approach, Recursive Bayesian approach or Naïve Bayesian approach.

Probabilistic approaches may use Bayesian likelihoods to consider two important factors to reach an accurate conclusion: (i) $P(t\ i/R)$ is the probability that an organism exhibiting test pattern R belongs to taxon t i, and (ii) $P(R/t\ i)$ is the probability that members of taxon t i will exhibit test pattern R. The minimal pattern within a sliding window integrated into the tools will assist investigators on "whether" and "how" organisms have been genetically modified.

Further variations encompassed within the systems and methods are described in the detailed description of the invention below.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

FIGS. 17A-17E illustrate the relative population measurements of 16S compared to the direct DNA sequencing with genomic identification of the present invention.

DETAILED DESCRIPTION OF PREFERRED EMBODIMENTS

Embodiments of the systems and methods for the characterization of populations of microorganisms in a sample are described herein with reference to the figures.

The methods and systems described in the current invention may use the shortest unique sequence information, which in a mixture of nucleic acids in an uncharacterized sample have the minimal unique length (n) with respect to the entire sequence information generated or collected. In addition to unique length sequences, non-unique may also be compared. The probability of identification of a genome increases with multiple matches. Some genomes will have longer minimal unique sequences than other genomes. The matching method of short length (n) sequences may continue in parallel with sequence information generation or collection. The comparisons occur as fast as (real-time) subsequent longer sequences are generated or collected. This results in considerable decision space reduction because the calculations are made early in terms of sequence information generation/collection. The probabilistic matching may include, but not limited to, perfect matching, subsequence uniqueness, pattern matching, multiple subsequence matching within n length, inexact matching, seed and extend, distance measurements and phylogenetic tree mapping. It may provide an automated pipeline to match the sequence information as fast as it is generated or in real-time. The sequencing instrument can continue to collect longer and more strings of sequence information in parallel with the comparison. Subsequent sequence information can also be compared and may increase the confidence of a genome or species identification in the sample. The method does not need to wait for sequence information assembly of the short reads into larger contigs.

In some embodiments, the system and methods may provide nucleic acid intake, isolation and separation, DNA sequencing, database networking, information processing, data storage, data display, and electronic communication to speed the delivery of relevant data to enable diagnosis or identification of organisms with applications for pathogenic outbreak and appropriate responses. In these embodiments, the system may include a portable sequencing device that electronically transmits data to a database for identification of organisms related to the determination of the sequence of nucleic acids and other polymeric or chain type molecules and probabilistic data matching.

Figure 1:
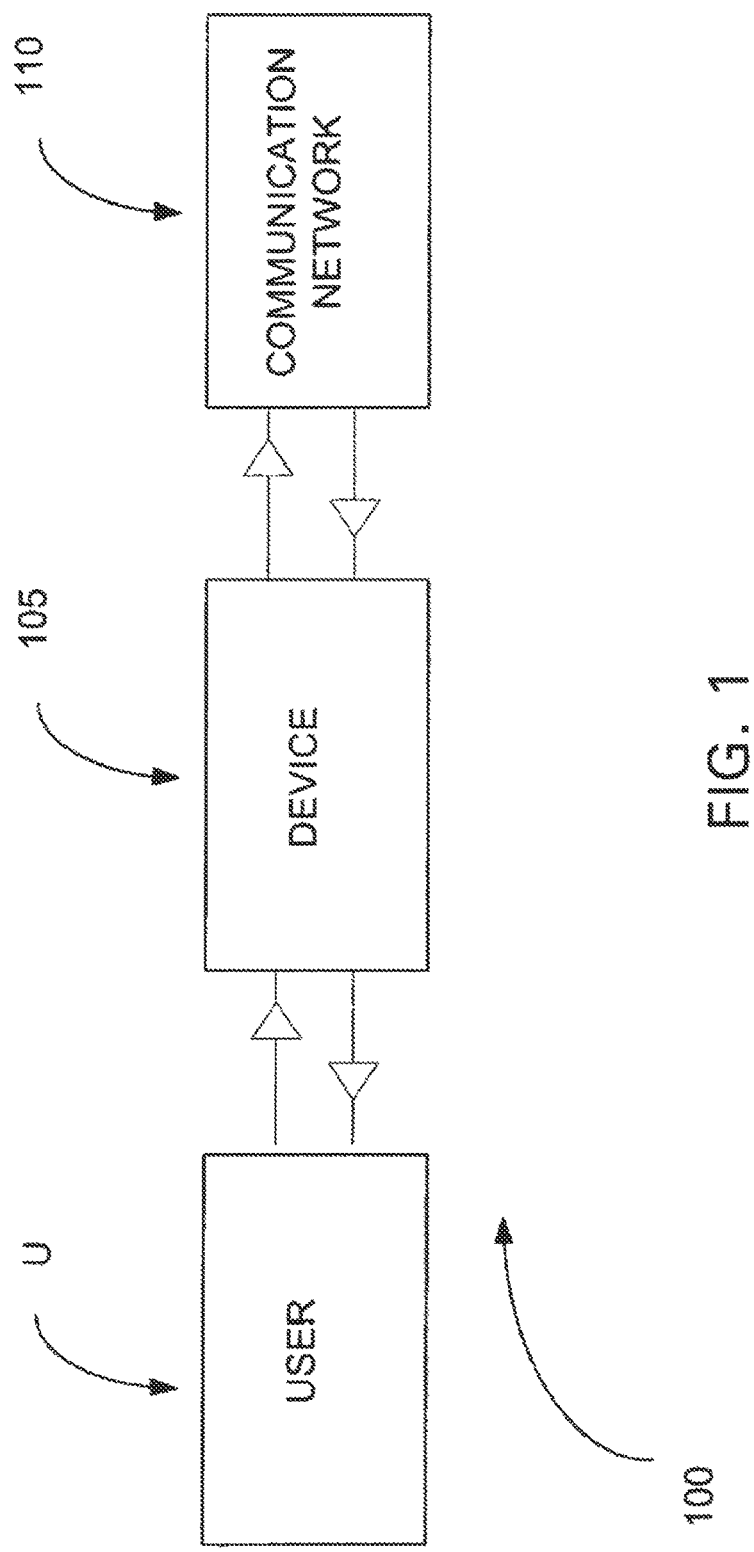
FIG. 1 is a schematic illustration of a disclosed system, which may be used for genomic ID of metagenomic samples at the species and strain level.
Figure 2:
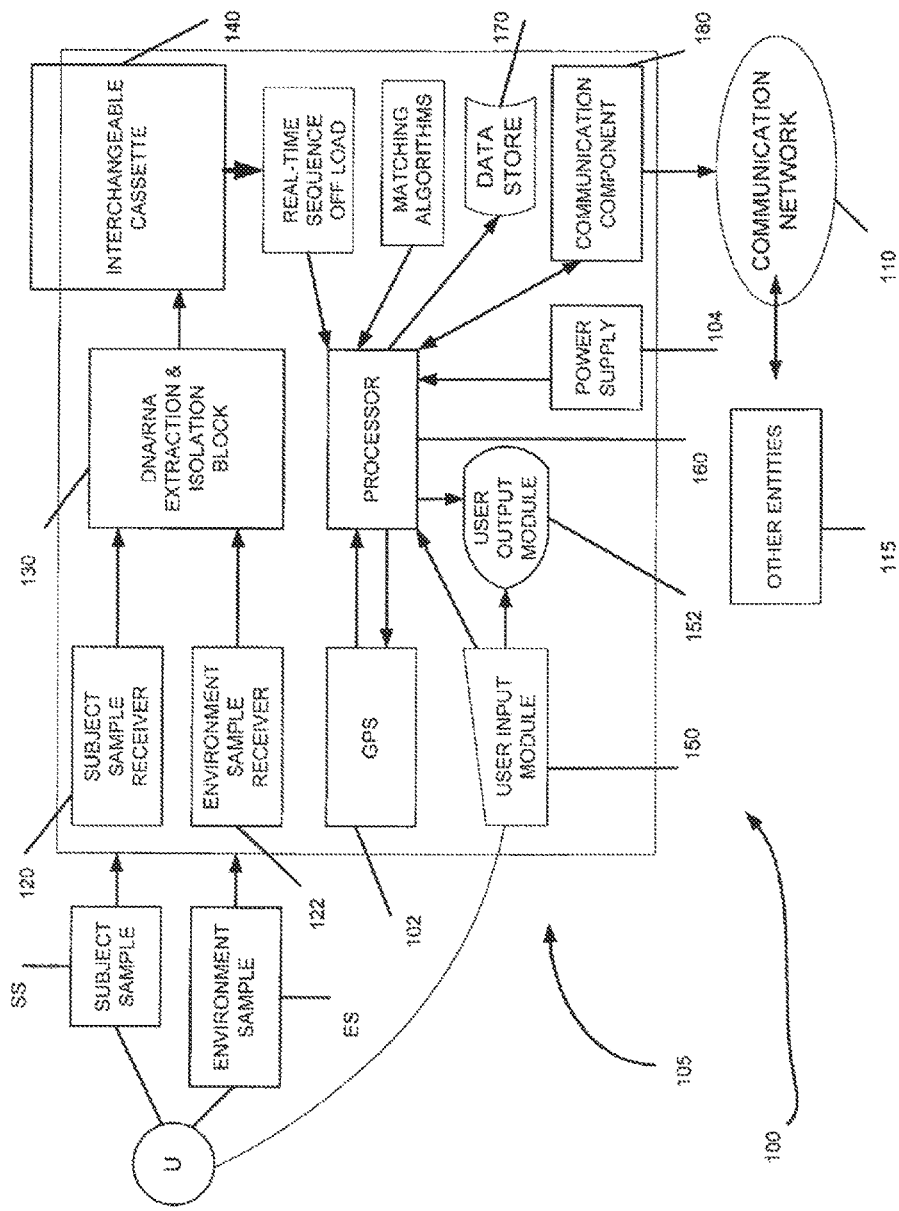
FIG. 2 is a more detailed schematic illustration of the system of FIG. 1.

FIGS. 1 and 2 illustrate an embodiment of a system 100 that includes a sequencing device 105, which may be a portable handheld electronic sequencing device. The sequencing device 105 may be configured to be readily held and used by a user (U), and may be capable of communicating via a communication network 110 with many other potentially relevant entities.

The device may be configured to receive a subject sample (SS) and an environment sample (ES), respectively. The subject sample (such as blood, saliva, etc), can include the subject's DNA as well as DNA of any organisms (pathogenic or otherwise) in the subject. The environment sample (ES) can include, but not limited to, organisms in their natural state in the environment (including food, air, water, soil, tissue). Both samples (SS, ES) may be affected by naturally occurring infection, an act of bioterrorism or by an emerging epidemic. Both samples (SS, ES) may be simultaneously collected via a tube or swab and may be received in a solution or solid (as a bead) on a membrane or slide, plate, capillary, or channel. The samples (SS, ES) may then be sequenced simultaneously. Circumstance specific situations may require the analysis of a sample composed of a mixture of the samples (SS, ES). A first responder can be contacted once a probabilistic match is identified and/or during real-time data collection and data interpretation. As time progresses an increasing percentage of the sequence can be identified.

Figure 3:
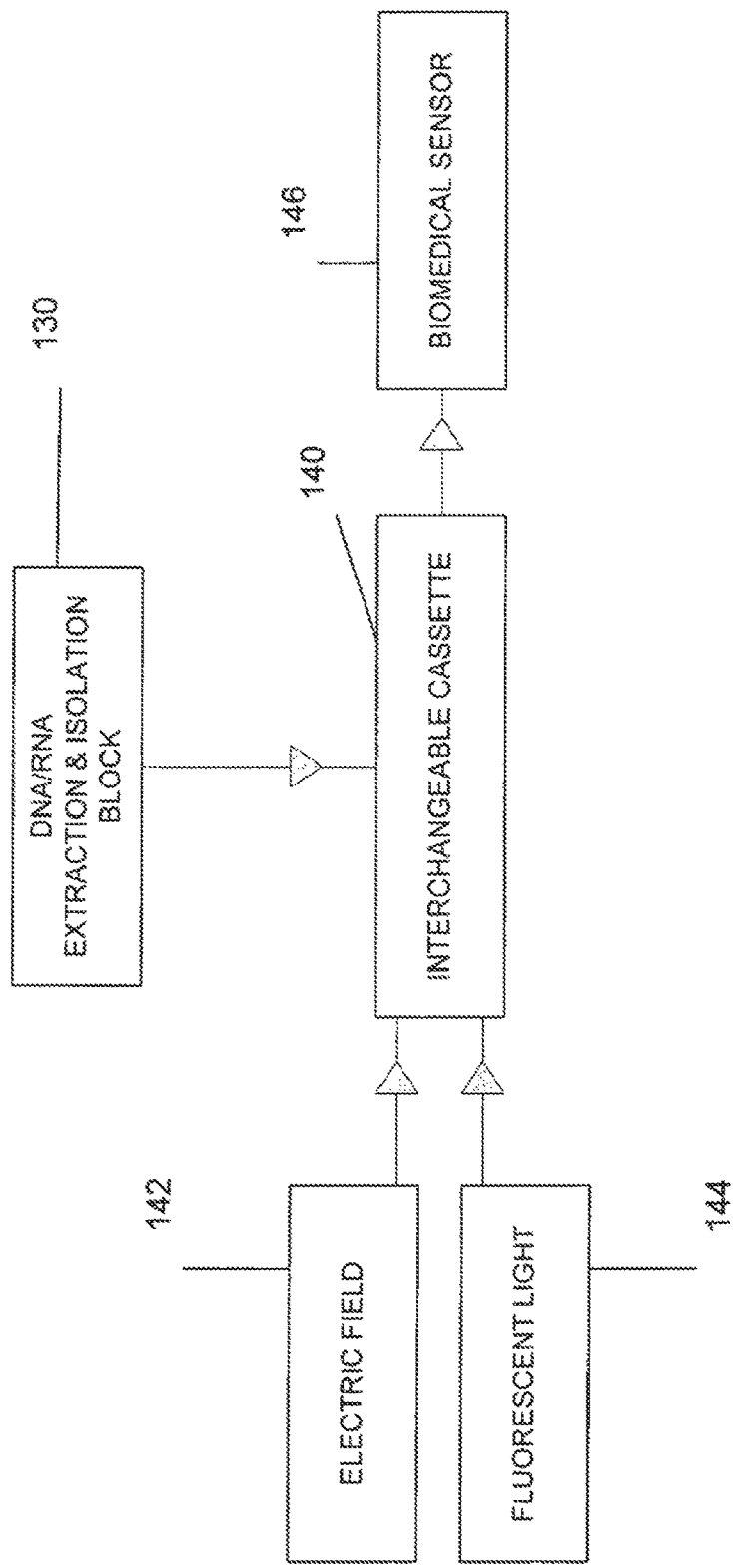
FIG. 3 is a schematic illustration of functional interaction between the interchangeable cassette and other components in an embodiment of the system of FIG. 1.

The sequencing device 105 may include the following functional components, as illustrated in FIG. 3, which enable the device 105 to analyze a subject sample (SS) and an environment sample (ES), communicate the resulting analysis to a communication network 110.

Sample receivers 120 and 122 may be coupled to a DNA Extraction and Isolation Block 130, which then deliver the samples to Block 130 via a flow system. Block 130 extracts DNA from the samples and isolates it so that it may be further processed and analyzed. This can be accomplished by use of a reagent template (i.e. a strand of DNA that serves as a pattern for the synthesis of a complementary strand of nucleic acid), which may be delivered combined with the samples 120, 122 using known fluidic transport technology. The nucleic acids in the samples 120, 122 are separated by the Extraction and Isolation Block 130, yielding a stream of nucleotide fragments or unamplified single molecules. An embodiment could include the use of amplification methods.

An interchangeable cassette 140 may be removeably coupled to sequencing device 105 and block 130. The cassette 140 can receive the stream of molecules from block 130 and can sequence the DNA and produce DNA sequence data.

The interchangeable cassette 140 can be coupled to, and provide the DNA sequence data to the processor 160, where the probabilistic matching is accomplished. An embodiment could include performance of 16 GB of data transferred at a rate of 1 Mb/sec. A sequencing cassette 140 is preferred to obtain the sequence information. Different cassettes representing different sequencing methods may be interchanged. The sequence information may be compared via probabilistic matching. Ultra-fast matching algorithms and pre-generated weighted signature databases may compare the de novo sequence data to stored sequence data.

The processor 160 can be, for example, an application-specific integrated circuit designed to achieve one or more specific functions or enable one or more specific devices or applications. The processor 160 can control all of the other functional elements of sequencing device 105. For example, the processor 160 can send/receive the DNA sequence data to be stored in a data store (memory) 170. The data store 170 can also include any suitable types or forms of memory for storing data in a form retrievable by the processor 160.

The sequencing device 105 can further include a communication component 180 to which the processor 160 can send data retrieved from the data store 170. The communication component 180 can include any suitable technology for communicating with the communication network 110, such as wired, wireless, satellite, etc.

The sequencing device 105 can include a user input module 150, which the user (U) can provide input to the device 105. This can include any suitable input technology such as buttons, touch pad, etc. Finally the sequencing device 105 can include a user output module 152 which can include a display for visual output and/or an audio output device.

The sequencing device 105 can also include a Global Positioning System (GPS) receiver 102, which can receive positioning data and proceed the data to the processor 160, and a power supply 104 (i.e. battery, plug-in-adapter) for supplying electrical or other types of energy to an output load or group of loads of the sequencing device 105.

The interchangeable cassette 140 is illustrated schematically in more detail in FIG. 3. The cassette 140 may be removeably coupled to sequencing device 105 and block 130 and includes a state of the art sequencing method (i.e. high throughput sequencing). Wet chemistry or solid state based system may be built on deck via a cassette exchangeable "plug & play" fashion. The cassette 140 can receive the stream of molecules from block 130 and can sequence the DNA via the sequencing method and can produce DNA sequence data. Embodiments include methods based on, but not limited to, Sequencing-by-synthesis, Sequencing-by-ligation, Single-molecule-sequencing and Pyrosequencing. A yet another embodiment of includes a source for electric field 142 and applies the electric field 142 to the stream of molecules to effect electrophoresis of the DNA within the stream. The cassette includes a light source 144 for emitting a fluorescent light 144 through the DNA stream. The cassette further includes a biomedical sensor (detector) 146 for detecting the fluorescent light emission and for detecting/determining the DNA sequence of the sample stream. In addition to fluorescent light, the biomedical sensor is capable of detecting light at all wavelengths appropriate for labeled moieties for sequencing.

The fluorescent detection comprises measurement of the signal of a labeled moiety of at least one of the one or more nucleotides or nucleotide analogs. Sequencing using fluorescent nucleotides typically involves photobleaching the fluorescent label after detecting an added nucleotide. Embodiments can include bead-based fluorescent, FRET, infrared labels, pyrophosphatase, ligase methods including labeled nucleotides or polymerase or use of cyclic reversible terminators. Embodiments can include direct methods of nanopores or optical waveguide including immobilized single molecules or in solution. Photobleaching methods include a reduced signal intensity, which builds with each addition of a fluorescently labeled nucleotide to the primer strand. By reducing the signal intensity, longer DNA templates are optionally sequenced.

Photobleaching includes applying a light pulse to the nucleic acid primer into which a fluorescent nucleotide has been incorporated. The light pulse typically comprises a wavelength equal to the wavelength of light absorbed by the fluorescent nucleotide of interest. The pulse is applied for about 50 seconds or less, about 20 seconds or less, about 10 seconds or less, about 5 seconds or less, about 2 seconds or less, about 1 seconds or less, or about 0. The pulse destroys the fluorescence of the fluorescently labeled nucleotides and/or the fluorescently labeled primer or nucleic acid, or it reduces it to an acceptable level, e.g., a background level, or a level low enough to prevent signal buildup over several cycles.

The sensor (detector) 146 optionally monitors at least one signal from the nucleic acid template. The sensor (detector) 146 optionally includes or is operationally linked to a computer including software for converting detector signal information into sequencing result information, e.g., concentration of a nucleotide, identity of a nucleotide, sequence of the template nucleotide, etc. In addition, sample signals are optionally calibrated, for example, by calibrating the microfluidic system by monitoring a signal from a known source.

As shown in FIG. 2, the sequencing device 105 can communicate via a communication network 110 with a variety of entities that may be relevant to notify in the event of a bioterrorist act or an epidemic outbreak. These entities can include a First Responder (i.e. Laboratory Response Network (i.e. Reference Labs, Seminal Labs, National Labs), GenBank®, Center for Disease Control (CDC), physicians, public health personnel, medical records, census data, law enforcement, food manufacturers, food distributors, and food retailers.

Figure 4:
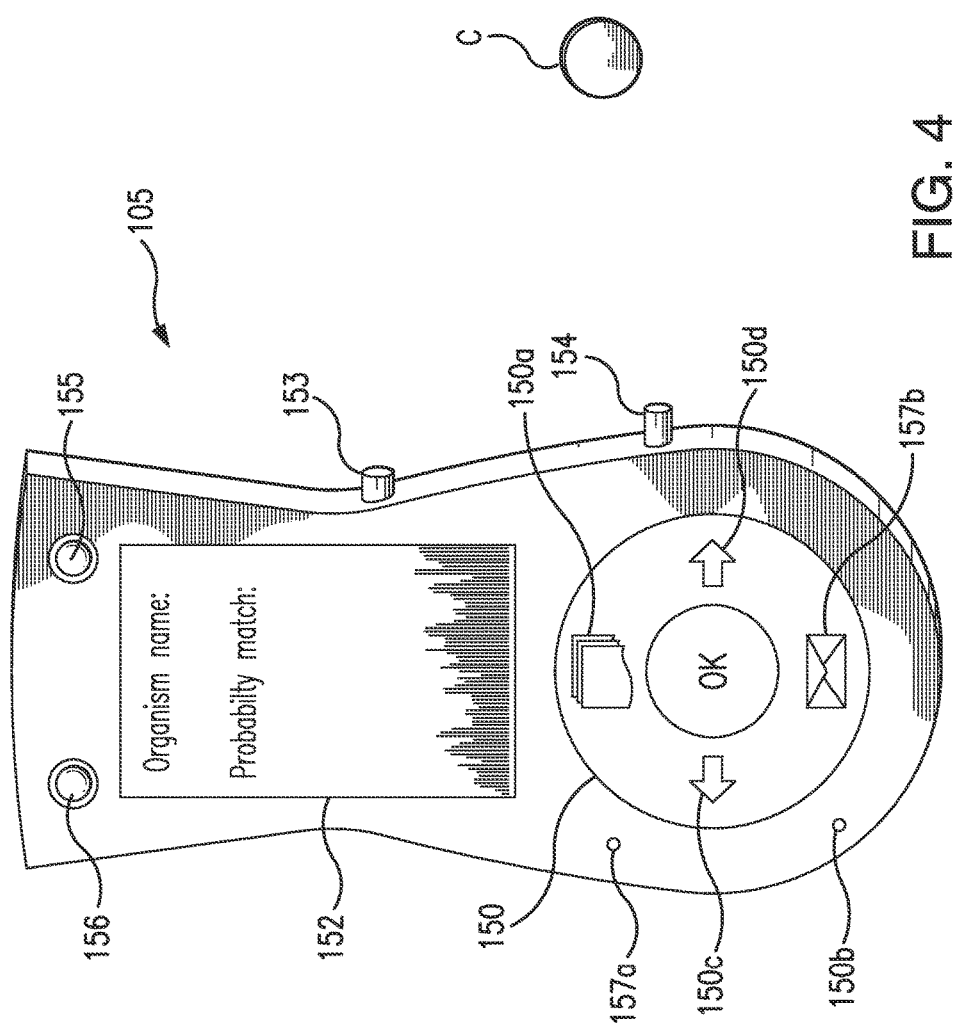
FIG. 4 is a front perspective view of an embodiment of a handheld electronic sequencing device, which may be used for genomic ID of metagenomic samples at the species and strain level.

One example embodiment of the sequencing device 105 discussed above is now described with reference to FIG. 4 illustrating an anterior view of the device. The device is a portable handheld sequencing device and is illustrated in comparison with the size of coins C. The device 105 is approximately 11 inches in length and easily transportable. (In FIG. 4, coins are shown for scale.) Two ports 153, 154 are located on a side of the device and represent sample receivers 120, 122. Port 153 is for receiving a subject sample (SS) or an environment sample (ES) to be analyzed and sequenced. Port 154 is for sequencing control (SC). The two different ports are designed to determine if a subject sample (SS) or environment sample (ES) contains materials that result in sequencing failure, should sequencing failure occur, or function in a CLIA capacity. The device 105 includes a user input module 150, which the user (U) can provide input to the device 105. In this particular embodiment, the user input module 150 is in the form of a touch pad, however, any suitable technology can be used. The touch pad includes buttons 150a for visual display, 150b, 150c for recording data, 150d for real-time data transmission and receiving, and 150e for power control for activating or deactivating the device. Alternatively, the key pad can be incorporated into the display screen and all functions can be controlled by liquid crystal interface. Suitable techniques are described in US Patent Pub. No. application 2007/0263163, the entire disclosure of which is hereby incorporated by reference. This can be by Bluetooth-enabled device pairing or similar approaches. The functions include digit keys, labeled with letters of the alphabet, such as common place on telephone keypads, such as a delete key, space key, escape key, print key, enter key, up/down, left/right, additional characters and any others desired by the user. The device further includes a user output module 152, in the form of a visual display, for displaying information for the user (U). An audio output device can also be provided if desired as illustrated at 157a and 157b. Finally, the sequencing device 105 includes light emitting diodes 155 and 156 to indicate the transmission or receiving of data. The function of the keys/buttons are to control all aspects of sample sequencing, data transmission and probabilistic matching and interface controls, including but not limited to on/off, send, navigation key, soft keys, clear, and LCD display functions and visualization tools with genome rank calculated by algorithms to list the confidence of matches. An embodiment includes an internet based system where multiple users may simultaneously transmit/receive data to/from a hierarchical network search engine.

Figure 5:
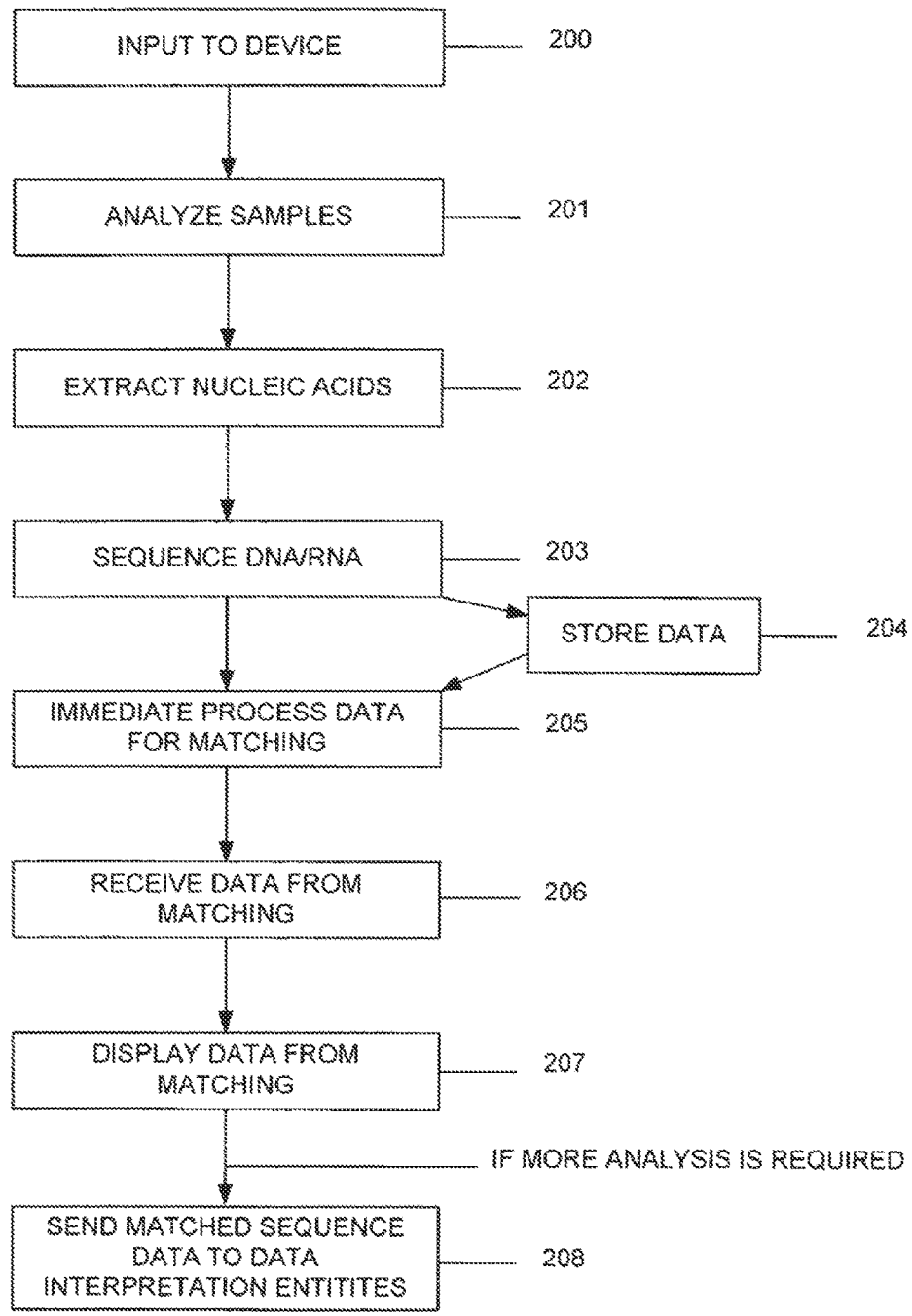
FIG. 5 is a flow chart illustrating a process of operation of the system of FIG. 1.

FIG. 5 is a flow chart illustrating a process of operation of the system 100 of an embodiment of the system 100 as described above. As shown in FIG. 5, a process of the device's operation includes at 200 receiving collected subject samples (SS) and environment sample (ES) in sample receivers 120, 122. At 202, the samples proceed to the DNA Extraction and Isolation Block 130 where the sample is analyzed and the DNA is extracted from the samples and isolated. At 203, the interchangeable cassette 140 receives the isolated DNA from block 130 and sequences the DNA. Depending on the cassette and if needed, with the application of an electric field 142 and of a fluorescent light 144, a biomedical sensor 146 within the cassette 140 detects/determines the DNA sequence of the sample stream. At 204, the sequenced data is processed and stored in a data store 170. At 205, the sequenced data is compared via probabilistic matching and genome identification is accomplished. The process is reiterative in nature. Resultant information may be transmitted via a communication network 110. GPS (global positioning system) data may optionally be transmitted as well at step 205. At 206, the device electronically receives data from matching. At 207, the device visually displays the data electronically received from matching via a user output module 152. If further analysis is require, at 208, the sequenced data is electronically transmitted to data interpretation entities (i.e. Public Health Personnel, Medical Records, etc.) via the communication network.

A multi-method research approach may enhance the rapid response to an incident and integrate primary care with organism detection. A triangulate response may be utilized, which involves quantitative instrument data from the DNA sequencing to converge with qualitative critical care. An infrastructure of observational checklists and audits of DNA sequencing data collected in the field across multiple locations may used to compare the appearance of an organism, e.g., bio-threat between locations. Inferential statistical analysis of the genomic data may be combined with medical observations to develop categories of priorities. Information collected and shared between databases of medical centers and genomic centers may enable triangulation of an incident, the magnitude of the incident, and the delivery of the correct intervention to the affected people at the appropriate time.

Figure 6:
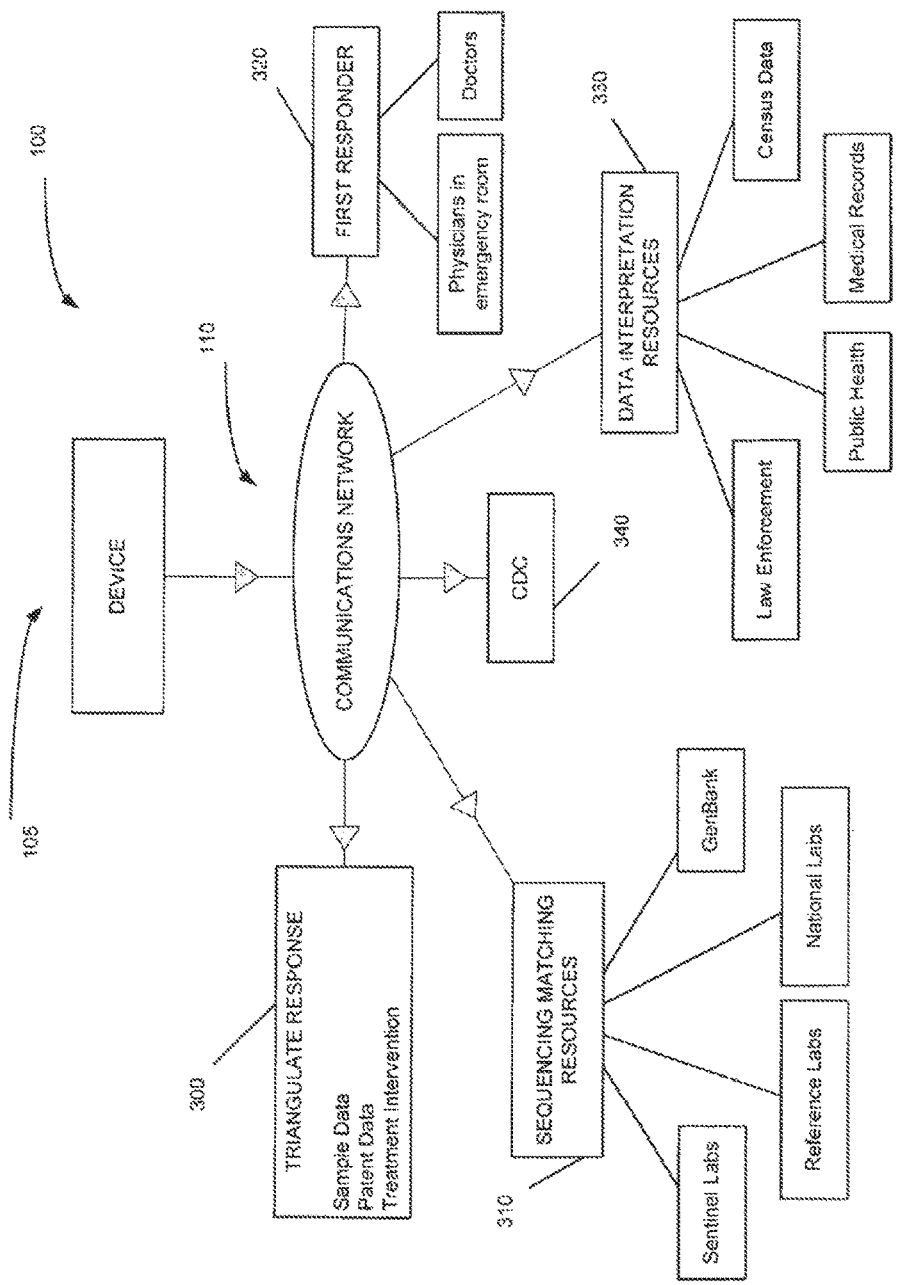
FIG. 6 is a schematic illustration of the interaction of the system of FIG. 1 with various entities potentially involved with the system.

FIG. 6 illustrates the interaction between the system 100 and various potential resources entities. The device 105 is configured to interact with these resource entities via a wireless or wired communication network. Device 105 can transmit triangulated sequenced data information (310) illustrating the "Sample Data", the "Patient Data", and "Treatment Intervention." Device 105 can transmit and receive DNA sequence data to and from sequence matching resources 320, which include GenBank® and a laboratory response network including Sentinel Labs, Reference Labs, and National Labs.

Each of the laboratories has specific roles. Sentinel laboratories (hospital and other community clinical labs) are responsible for ruling out or referring critical agents that they encounter to nearby LRN reference laboratories. Reference laboratories (state and local public health laboratories where Biological Safety Level 3 (BSL-3) practices are observed) perform confirmatory testing (rule in). National laboratories (BSL-4) maintain a capacity capable of handling viral agents such as Ebola and variola major and perform definitive characterization.

System 100 can further transmit and receive data to and from Data Interpretation Resources 330 including law enforcement entities, public health personnel, medical records, and census data. Finally, the device 105 can transmit and receive data to and from a first responder 320 which include doctors or physicians in an emergency room. The system 100 overall is configured to communicate with the Center for Disease Control (CDC) 340 to provide pertinent information to the proper personnel.

Figure 7:
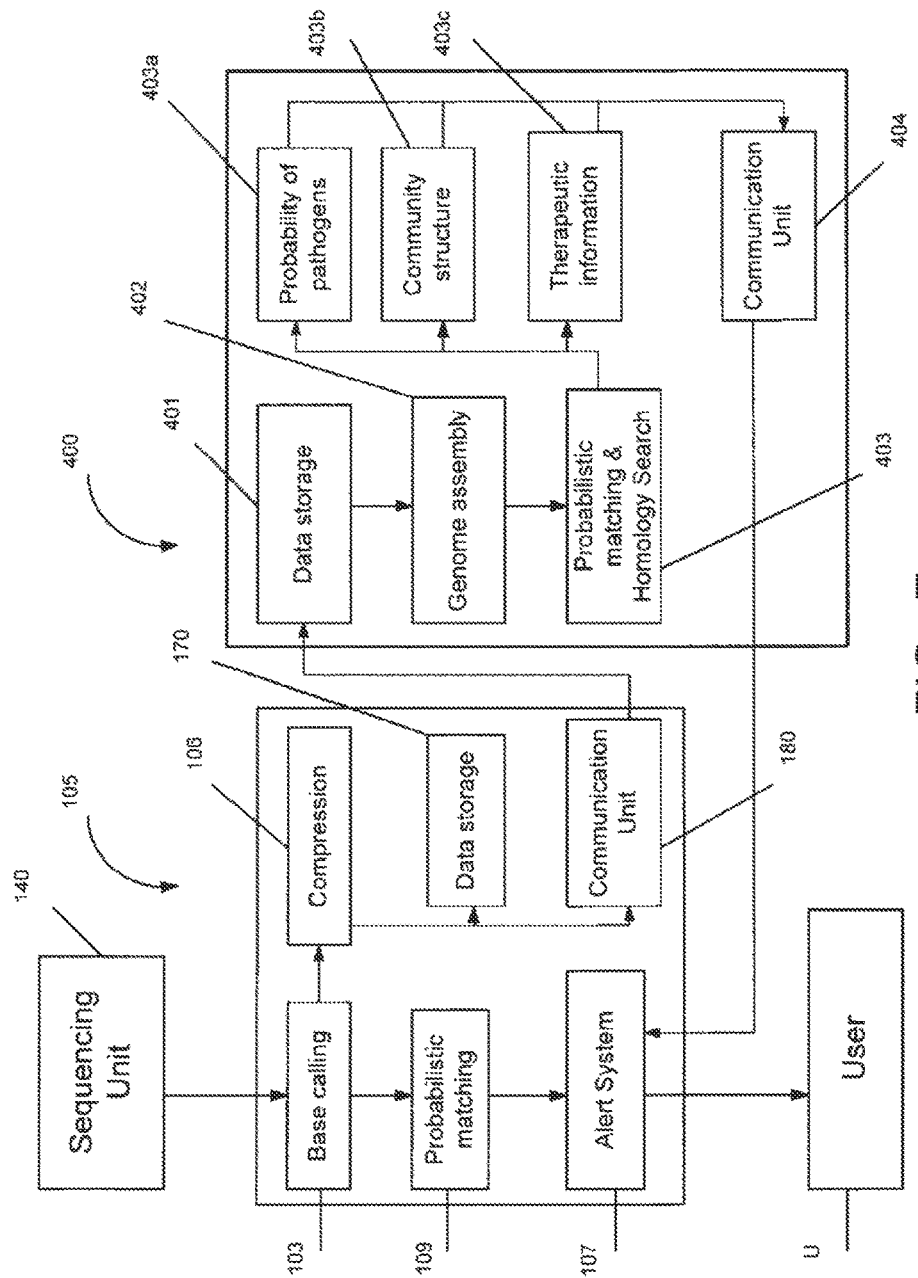
FIG. 7 is a schematic illustration of functional interaction between a hand held electronic sequencing device with the remote analysis center.

FIG. 7 is a schematic illustration of functional interaction between a hand held electronic sequencing device with the remote analysis center. The device 105 may include a base calling unit 103 for processing sequencing received by the interchangeable cassette 140. Such sequences and SNP sites are individually weighted according to its probability found in each species. These weights can be calculated either theoretically (by simulation) or experimentally. The device also includes a probabilistic matching processor 109 coupled to the base calling unit 103. The probabilistic matching may be performed in real time or as fast as the sequence base calling or sequence data collection. The probabilistic matching processor 109, using a Bayesian approach, can receive resultant sequence and quality data, and can calculate the probabilities for each sequencing-read while considering sequencing quality scores generated by the base calling unit 103. The probabilistic matching processor 109 can use a database generated and optimized prior to its use for the identification of pathogens. An alert system 107 is coupled to the probabilistic matching processor 109 and can gather information from the probabilistic matching processor 109 (on site) and display the best matched organism(s) in real-time.

The alert system 107 is configured to access patient data, i.e. the medical diagnosis or risk assessment for a patient particularly data from point of care diagnostic tests or assays, including immunoassays, electrocardiograms, X-rays and other such tests, and provide an indication of a medical condition or risk or absence thereof. The alert system can include software and technologies for reading or evaluating the test data and for converting the data into diagnostic or risk assessment information. Depending on the genome identity of the bio-agent and the medical data about the patient, an effective "Treatment Intervention" can be administered. The treatment can be based on the effective mitigation or neutralization of the bio-agent and/or its secondary effects and based on the patient history if there are any contra-indications. The alert system can be based on the degree and number of occurrences. The number of occurrences can be based on the genomic identification of the bio-agent. A value can be pronounced when the result is within or exceeds a threshold as determined by government agencies, such as the CDC or DoD or Homeland Security. The alert system is configured to enable clinicians to use the functionality of genomic identification data with patient data. The communication permits rapid flow of information and accurate decision making for actions by first responders or other clinical systems.

The device 105 further includes a data compressor 106 coupled to the base calling unit 103, configured to receive the resultant sequence and quality data for compression. The data store 170 is coupled to the compressor 106 and can receive and store the sequence and quality data.

The sequencing device 105 interacts with a remote analysis center 400, which can receive electronically transferred data from the communication component 180 of the sequencing device 105 via a wired and/or wireless communication method. The remote analysis center 400 contains a large sequence database including all of nucleotide and amino acid sequences and SNP data available to date. This database also contains associated epidemiological and therapeutic information (e.g. antibiotic resistance). The remote analysis center 400 further includes a data store 401. The data store 401 can receive decompressed sequence data information via electronic transmission from the communication component 180 of the sequencing device 105. A genome assembly 402 is coupled to the data store 401 and can and assemble the decompressed sequence data. Obvious contaminant DNA, such as human DNA, can be filtered prior to further analysis.

The remote analysis center 400 further includes a processor 403 equipped with probabilistic matching technology and homology search algorithms, which can be employed to analyze assembled sequence data to obtain the probabilities of the presence of target pathogens 403a, community structure 403b, epidemiological and therapeutic information 403c. Genome sequence data of target pathogens are compared with those of genomes of non-pathogens including human and metagenome to identify nucleotide sequences and single nucleotide polymorphic (SNP) sites, which only occur in target organisms. The analysis at the remote analysis center 400 is carried out on the fly during data transfer from the sequencing device 105. The remote analysis center 400 can further include a communication unit 404 from which the analysis results are electronically transferred back to the alert system 107 within the sequencing device 105 as well as other authorities (e.g. DHS, CDC etc.).

Probabilistic Classification: The present invention may provide database engines, database design, filtering techniques and the use of probability theory as Extended Logic. The instant methods and system may utilize the probability theory principles to make plausible reasoning (decisions) on data produced by nucleic acid sequencing. Using the probability theory approach, the system described herein may analyze data as soon as it reaches a minimal number of nucleotides in length (n), and calculating the probability of the n-mer, further each subsequent increase in length (n+base pair(s)) is used to calculate the probability of a sequence match. The calculation of each n-mer and subsequent longer n-mers may be further processed to recalculate the probabilities of all increasing lengths to identify the presence of genome(s). As the unit length increases, multiple sub-units, within the n-mer are compared for pattern recognition, which further increases the probability of a match. Such method, including other Bayesian methods, provides for eliminating matches and identifying a significant number of biological samples comprising with a very short nucleotide fragment or read without having to complete full genome sequencing or assembling the genome. As such assigning the likelihood of the match to existing organisms and move on to the next nucleic acid sequence read to further improve the likelihood of the match. The system described herein increases speed, reduces reagent consumption, enables miniaturization, and significantly reduces the amount of time required to identify the organism.

In order to build probabilistic classifiers to make a decision on short nucleic acid sequences, a variety of approaches to first filter and later classify the incoming sequencing data can be utilized. In the instant case, the formalism of Bayesian networks is utilized. A Bayesian network is a directed, acyclic graph that compactly represents a probability distribution. In such a graph, each random variable is denoted by a node (for example, in a phylogenetic tree of an organism). A directed edge between two nodes indicates a probabilistic dependency from the variable denoted by the parent node to that of the child. Consequently, the structure of the network denotes the assumption that each node in the network is conditionally independent of its non-descendants given its parents. To describe a probability distribution satisfying these assumptions, each node in the network is associated with a conditional probability table, which specifies the distribution over any given possible assignment of values to its parents. In this case a Bayesian classifier is a Bayesian network applied to a classification task of calculating the probability of each nucleotide provided by any sequencing system. At each decision point the Bayesian classifier can be combined with a version of shortest path graph algorithm such as Dijkstra's or Floyd's.

The current system may implement a system of Bayesian classifiers (for example, Naïve Bayesian classifier, Bayesian classifier and Recursive Bayesian estimation classifier) and fuse the resulting data in the decisions database. After the data is fused, each classifier may be fed a new set of results with updated probabilities.

Figure 8:
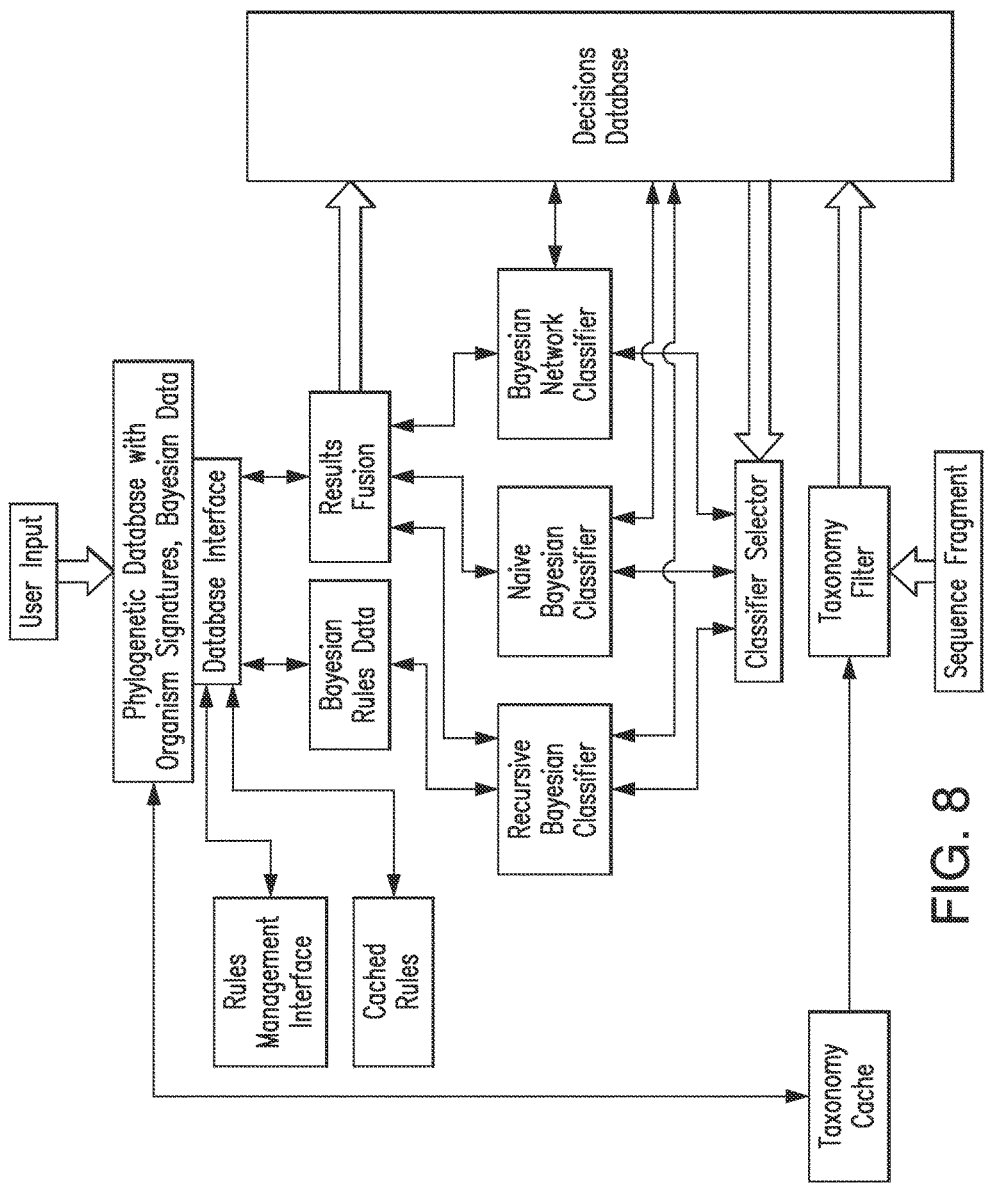
FIG. 8 is a schematic illustration of the overall architecture of the probabilistic software module.
Figure 9:
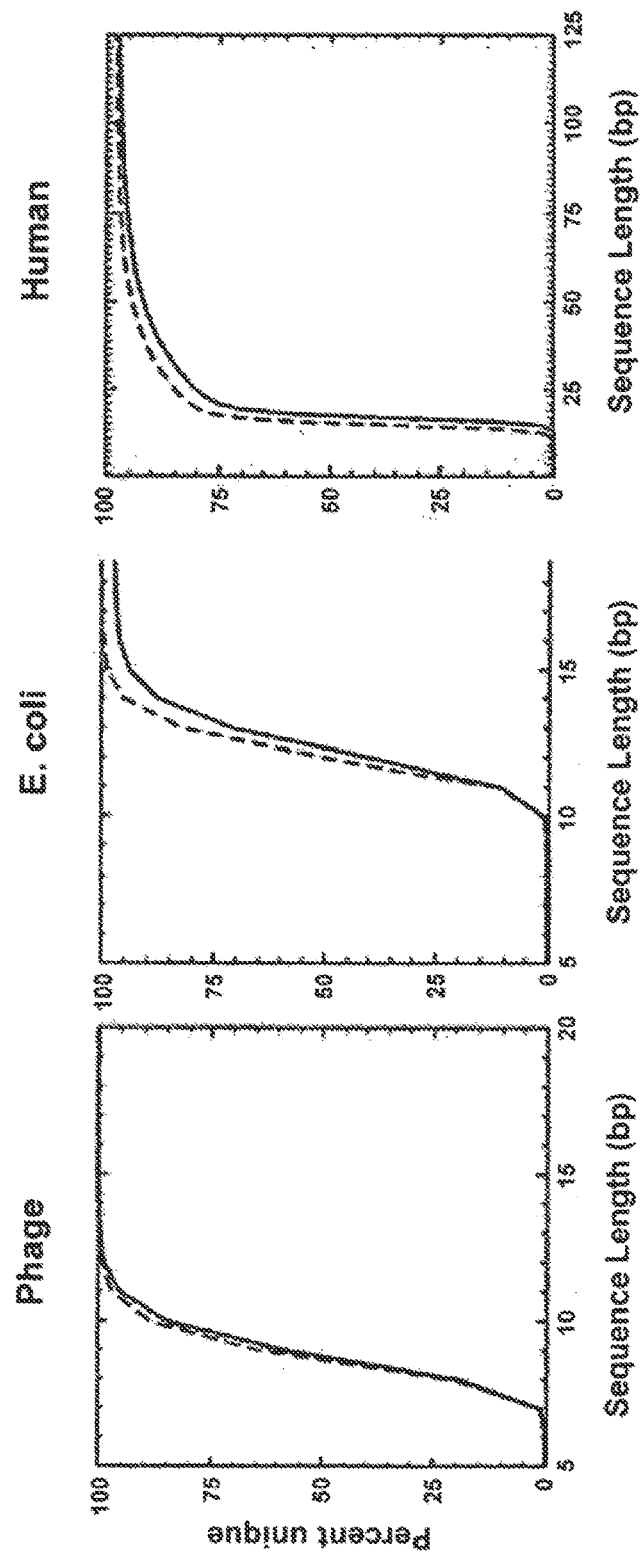
FIG. 9 shows the percentage of unique sequences as a function of read length.
Figure 10:
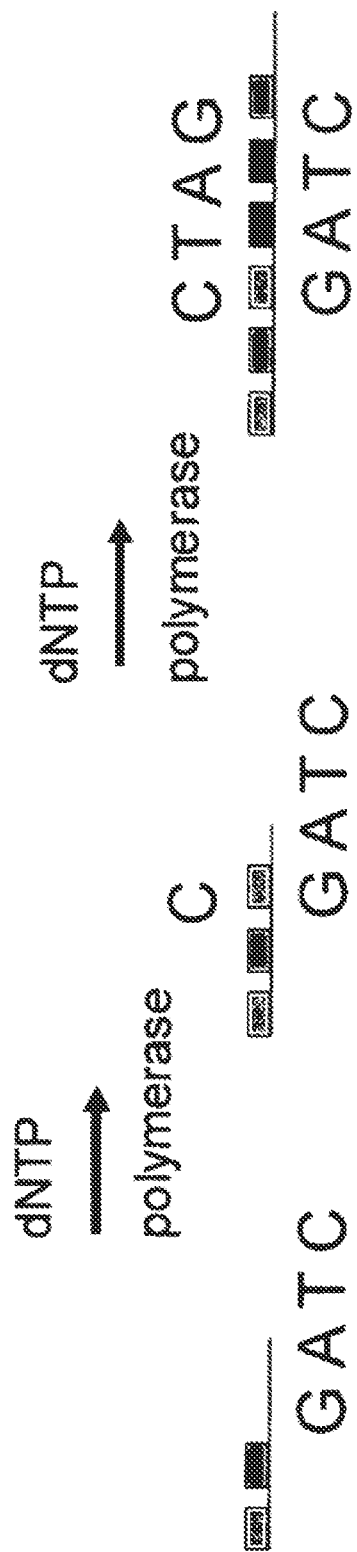
FIG. 10 is a summary of principle steps of sequencing.

FIG. 8 shows a schematic illustration of the overall architecture of the probabilistic software module.

DNA Sequencing Fragment: Any sequencing method can be used to generate the sequence fragment information. The module, 160 in FIG. 2 or 109 in FIG. 7 is responsible for processing data incoming from Sequencing module in the interchangeable cassette. The data is encapsulated with sequencing data as well as information above start and stop of the sequence, sequence ID, DNA chain ID. The module formats the data and passes it to the taxonomy filter module. The formatting includes addition of the system data and alignment in chunks.

DNA Sequencing module has 2 interfaces. It is connected to DNA Prep module and to taxonomy Filter.

I. DNA Prep Interface: Several commercially available methods to accomplish sample preparation can be integrated via microfluidics techniques. Typical sample preparation is solution based and includes cell lysis and inhibitor removal. The nucleic acids are recovered or extracted and concentrated. Embodiments of the lysis include detergent/enzymes, mechanical, microwave, pressure, and/or ultrasonic methods. Embodiments of extraction include solid phase affinity and/or size exclusion.

II. Taxonomy Filter: Taxonomy filter has two main tasks: (i) Filter out as many organisms as possible to limit the classifier module to a smaller decision space, and (ii) Help determine the structure of the Bayesian network, which involves the use of machine learning techniques.

Phylogenetic tree filter: This sub-module of taxonomy filter interfaces with "Decisions Database" to learn the results of the previous round of analysis. If no results are found the module passes the new data to classification module. If the results are found the taxonomy filter adjusts classifier data to limit the possible decision space. For example if the prior data indicates that this is a virus DNA sequence that is being looked at, the decision space for the classifier will be shrunk to viral data only. This can be done by modifying the data Bayesian classifiers collected while operating.

Machine Learning: Machine learning algorithms are organized into a taxonomy, based on the desired outcome of the algorithm. (i) Supervised learning—in which the algorithm generates a function that maps inputs to desired outputs. One standard formulation of the supervised learning task is the classification problem: the learner is required to learn (to approximate) the behavior of a function which maps a vector [X1, X2, . . . XN] into one of several classes by looking at several input-output examples of the function. (ii) Semi-supervised learning—which combines both labeled and unlabeled examples to generate an appropriate function or classifier. (iii) Reinforcement learning—in which the algorithm learns a policy of how to act given an observation of the world. Every action has some impact in the environment, and the environment provides feedback that guides the learning algorithm. (iv) Transduction—predicts new outputs based on training inputs, training outputs, and test inputs which are available while training. (v) Learning to learn—in which the algorithm learns its own inductive bias based on previous experience.

Taxonomy Cache Module: The module caches taxonomy information produced by taxonomy filter. It can act as an interface between taxonomy filter and taxonomy database which holds all of the information in SQL database. Taxonomy cache is implemented as in-memory database with micro-second response timing. Queries to the SQL database are handled in a separate thread from the rest of the sub-module. Cache information includes the network graph created by the taxonomy filter module. The graph contains the whole taxonomy as the system starts analysis. DNA sequence analysis reduces the taxonomy graph with taxonomy cache implementing the reductions in data size and the removal of the appropriate data sets.

Classifier Selector: The instant system can utilize multiple classification techniques executing in parallel. Classifier selector can act as data arbiter between different classification algorithms. Classifier selector can reads information from the Decisions Database and push such information to the classification modules with every DNA sequencing unit received for analysis from DNA Sequencing Module. Taxonomy filter acts as data pass through for the DNA sequencing data.

Recursive Bayesian Classifier: Recursive Bayesian classifier is a probabilistic approach for estimating an unknown probability density function recursively over time using incoming measurements and a mathematical process model. The module receives data from classifier selector and from the Decisions Database where prior decisions are stored. The data set is retrieved from the databases and prior decision identification placed in local memory of the module where the filtering occurs. The classifier takes DNA sequence and tries to match it with or without existing signatures, barcodes, etc., from the taxonomy database by quickly filtering out families of organisms that do not match. The algorithm works by calculating the probabilities of multiple beliefs and adjusting beliefs based on the incoming data. Algorithms used in this module may include Sequential Monte Carlo methods and sampling importance resampling. Hidden Markov Model, Ensemble Kalman filter and other particle filters may also be used together with Bayesian update technique.

Naïve Bayesian Classifier: Simple probabilistic classifier based on the application of the Bayes' theorem. The classifier makes all decisions based on the pre-determined rule-set which is provided as user input at start-up. The module can be re-initialized with a new rule set while it is executing analysis. New rules set can come from the user or it can be a product of the rules fusion of The Results Fusions module.

Bayesian Network Classifier: Bayesian Network Classifier implements a Bayesian network (or a belief network) as a probabilistic graphical model that represents a set of variables and their probabilistic independencies.

Decisions Database: Decisions Database is a working cache for most modules in the system. Most modules have direct access to this resource and can modify their individual regions. However only Results Fusion module can access all data and modify the Bayesian rule sets accordingly.

Bayesian Rules Data: The module collects all Bayesian rules in binary, pre-compiled form. The rules are read-write to all Bayesian classifiers as well as Taxonomy Filter and Results Fusions modules. The rules are dynamically recompiled as changes are made.

Results Fusion The module fuses the date from multiple Bayesian classifiers as well as other statistical classifiers that are used. Results Fusion module looks at the mean variance between generated answers for each classifier and fuses the data if needed.

Database Interface: Interface to the SQL database. The interface is implemented programmatically with read and write functions separated in different threads. MySQL is the database of choice however sqLite may be used for faster database speed.

Taxonomy Database: The database will hold multiple internal databases: taxonomy tree, indexed pre-processed tree, user input and rules.

Cached Rules In-Memory cache of post-processed rules provided by the user.

Rules Management: Graphical Management Interface to the Module

User Input: User created inference rules. The rules are used by Bayesian classifiers to make decisions.

The systems and methods of the invention are described herein as being embodied in computer programs having code to perform a variety of different functions. The code may be embodied on a non-transitory computer readable medium. Particular best-of-class technologies (present or emerging) can be licensed components. Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426, 4,923,978, EP Patents 0512767 A1 and EP 0515484B and WO 95/13368, WO 97/10331 and WO 96/18731, the entire disclosures of which are hereby incorporated by reference. It should be understood, however, that the systems and methods are not limited to an electronic medium, and various functions can be alternatively practiced in a manual setting. The data associated with the process can be electronically transmitted via a network connection using the Internet. The systems and techniques described above can be useful in many other contexts, including those described below.

Disease association studies: Many common diseases and conditions involve complex genetic factors interacting to produce the visible features of that disease, also called a phenotype. Multiple genes and regulatory regions are often associated with a particular disease or symptom. By sequencing the genomes or selected genes of many individuals with a given condition, it may be possible to identify the causative mutations underlying the disease and relationship of specific disease causing agents to the condition(s). This research may lead to breakthroughs in disease detection, prevention and treatment.

Cancer research: Cancer genetics involves understanding the effects of inherited and acquired mutations and other genetic alterations. The challenge of diagnosing and treating cancer is further compounded by individual patient variability and hard-to-predict responses to drug therapy. The availability of low-cost genome sequencing to characterize acquired changes of the genome that contribute to cancer based on small samples or tumor cell biopsies, and identification of infectious agents associated with and/or influencing the disease diagnosis, prognosis, and outcome may enable improved diagnosis and treatment of cancer.

Pharmaceutical research and development: One promise of genomics has been to accelerate the discovery and development of more effective new drugs. The impact of genomics in this area has emerged slowly because of the complexity of biological pathways, disease mechanisms and multiple drug targets. Single molecule sequencing could enable high-throughput screening in a cost-effective manner using large scale gene expression analysis to better identify promising drug leads. In clinical development, the disclosed technology could potentially be used to generate individual gene profiles that can provide valuable information on likely response to therapy, toxicology or risk of adverse events, and possibly to facilitate patient screening and individualization of therapy.

Infectious disease: All viruses, bacteria and fungi contain DNA or RNA. The detection and sequencing of DNA or RNA from pathogens at the single molecule level could provide medically and environmentally useful information for the diagnosis, treatment and monitoring of infections and to predict potential drug resistance.

Autoimmune conditions: Several autoimmune conditions, ranging from multiple sclerosis and lupus to transplant rejection risk, are believed to have a genetic component. Monitoring the genetic changes and probable microorganisms associated with these diseases may enable better patient management.

Clinical diagnostics: Patients who present the same disease symptoms often have different prognoses and responses to drugs based on their underlying genetic differences. Delivering patient-specific genetic information encompass molecular diagnostics including gene- or expression-based diagnostic kits and services, companion diagnostic products for selecting and monitoring particular therapies, as well as patient screening for early disease detection and disease monitoring. Creating more effective and targeted molecular diagnostics and screening tests requires a better understanding of genes, regulatory factors and other disease- or drug-related factors, as well as associated or causative microbial agents, which the disclosed single molecule sequencing technology has the potential to enable.

Agriculture: Agricultural research has increasingly turned to genomics for the discovery, development and design of genetically superior animals and crops. The agribusiness industry has been a large consumer of genetic technologies—particularly microarrays—to identify relevant genetic variations across varieties or populations. The disclosed sequencing technology may provide a more powerful, direct and cost-effective approach to gene expression analysis and population studies and identification of commensal, pathogenic, and/or symbiotic microbial agents for this industry.

Further opportunity will be in the arena of repeat-sequence applications where the methods are applied to the detection of subtle genetic variation. Expanded comparative genomic analysis across species may yield great insights into the structure and function of the human genome and, consequently, the genetics of human health and disease and relationships of microorganisms to human health or disease. Studies of human genetic variation and its relationship to health and disease are expanding. Most of these studies use technologies that are based upon known, relatively common patterns of variation. These powerful methods will provide important new information, but they are less informative than determining the full, contiguous sequence of individual human genomes. For example, current genotyping methods are likely to miss rare differences between people at any particular genomic location and have limited ability to determine long-range rearrangements. Characterization of somatic changes of the genome that contribute to cancer currently employ combinations of technologies to obtain sequence data (on a very few genes) plus limited information on copy number changes, rearrangements, or loss of heterozygosity. Such studies suffer from poor resolution and/or incomplete coverage of the genome. The cellular heterogeneity of tumor samples presents additional challenges as well as lack of knowledge of human aminoflora. Low cost complete genome sequencing from exceedingly small samples, perhaps even single cells, would alter the battle against cancer in all aspects, from the research lab to the clinic. The recently-launched Cancer Genome Atlas (TCGA) pilot project moves in the desired direction, but remains dramatically limited by sequencing costs. Additional genome sequences of agriculturally important animals and plants are needed to study individual variation, different domesticated breeds and several wild variants of each species. Sequence analysis of microbial communities, many members of which cannot be cultured, will provide a rich source of medically and environmentally useful information. And accurate, rapid sequencing may be the best approach to microbial monitoring of food and the environment, including rapid detection and mitigation of bioterrorism threats.

Genome Sequencing could also provide isolated nucleic acids comprising intronic regions useful in the selection of Key Signature sequences. Currently, Key Signature sequences are targeted to exonic regions.

A fundamental application of DNA technology involves various labeling strategies for labeling a DNA that is produced by a DNA polymerase. This is useful in microarray technology: DNA sequencing, SNP detection, cloning, PCR analysis, and many other applications.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

Example 1

Purpose: The use of key signatures and/or bar codes to enable genome identification with as few as 8-18 nucleotides and analysis of very short sequence data (reads) in real-time.

Linear time suffix array construction algorithms were used to calculate the uniqueness analysis. The analysis determined the percentage of all sequences that were unique in several model genomes. All sequence lengths in a genome were analyzed. Sequences that occur only once in a genome are counted. The suffix array algorithm works by calculating a repeat score plot which analyzes the frequency of specific subsequences within a sequence to occur based on a two base pair sliding window. Genome information stored in GenBank was used for the in-silico analysis. A viral genome, Lambda-phage, a bacterial genome, *E. coli* K12 MG1655, and the human genome were analyzed. The percentage of unique reads is a function of sequence length. An assumption was made concerning the sequences that only produce unambiguous matches and which produce unambiguous overlaps to reconstruct the genome. Unique reads ranged in size from 7 to 100 nucleotides. The majority of unique sizes were shorter than 9, 13, and 18 nucleotides, respectively.

Results: The results show that random sequences of 12 nt of the phage genome are 98% unique to phage. This increases slowly such that 400 nt (nucleotide) sequences are 99% unique to phage. This decreases to 80% for phage sequences of 10 nt. For bacteria (*E. coli*) sequences of 18 nt of the genome are 97% unique to *E. coli*. For Human genomes, sequences of 25 nt are 80% unique to human and an increase to 45 nt results in 90% of the genome as unique.

As noted above, although the present invention has been described with embodiments and examples, the breadth and scope of the invention should not be limited by any of the above-described embodiments. For example, although embodiments of the invention in which identification of genomes present in biological material of a sample occurred instantly or in real-time and with direct communication with a sequencer may have been described, the present invention does not require the identification to occur instantly or in real-time or direct communication or contact with a sequencer. However, probabilistic matching to identify metagenomic fragments against a genomic database may be performed separately from sequencing at a later time using an output file generated by a sequencer, and no direct communication or processing connected to the sequencer is required. Thus, although the identification may be performed in parallel (i.e., in-line) with sequencing of the biological material as described, this is also not necessary and the identification may be performed in a step-wise fashion. In fact, each of the steps of sample collection, sample extraction, sequencing and identification may be performed separately and in a step-wise fashion. Further, in regard to the sequencer used in or with the present invention, there is no requirement that the sequencer be portable or handheld.

Figure 11:
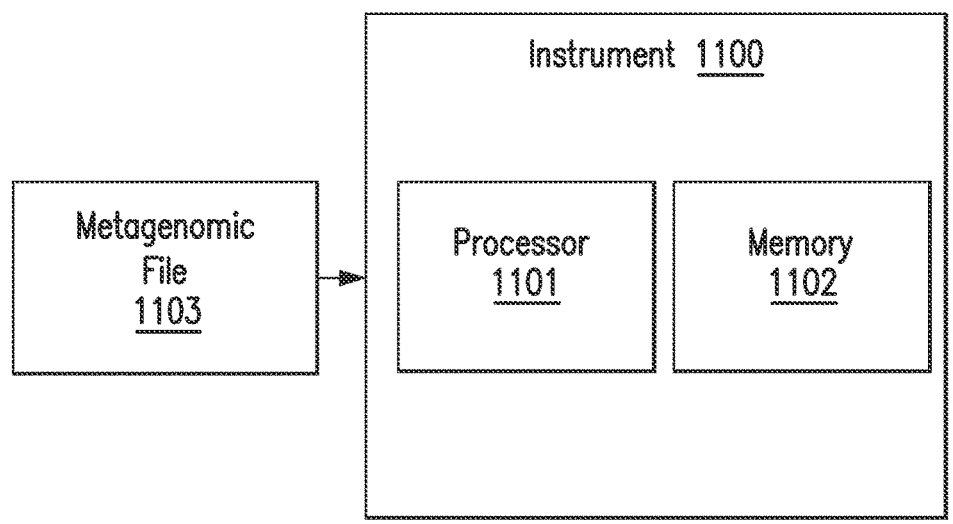
FIG. 11 is a schematic illustration of an instrument capable of characterizing populations of microorganisms in a sample according to one embodiment of the present invention.

FIG. 11 is a schematic illustration of an instrument 1100 according to one embodiment of the present invention. Instrument 1100 may be a device capable of characterizing populations of microorganisms in a sample. In particular, instrument 1100 may be a device capable of characterizing the identities and relative populations of microorganisms, such as pathogens and commensals, in a sample at the species and/or sub-species (e.g., morphovars, serovars, and biovars) level and/or strain level.

Instrument 1100 may comprise a processor 1101 and a memory 1102 configured to perform the characterization of populations of microorganisms in a sample. Alternatively, instrument 1100 may comprise units in the form of hardware and/or software each configured to perform one or more portions of the characterization of populations of microorganisms in a sample. Further, each of the units may comprise its own processer and memory, or each of the units may share a processor and memory with one or more of the other units.

Instrument 1100 utilizes metagenomic fragment reads, which may be produced by collecting a sample, extracting metagenomic fragments (e.g., nucleic acid and/or protein and/or metabolites), and sequencing the fragments. The sample may contain a plurality of microbial organisms, including bacteria, viruses, parasites, fungi, plasmids and other exogenous DNA or RNA fragments available in the sample type. Instrument 1100 may utilize hundreds, thousands or millions of short metagenomic fragment reads. The metagenomic fragment reads may be in the form of a metagenomic file 1103 produced from the metagenomic fragment reads.

Although the present invention may utilize metagenomic fragment reads that may be greater than 100 base pairs in length, the metagenomic fragment reads utilized may also have lengths of approximately 12 to 100 base pairs. For instance, instrument 1100 may characterize populations of microorganisms using metagenomic fragment reads having lengths of approximately 12 to 15 base pairs, 16 to 25 base pairs, 25 to 50 base pairs or 50 to 100 base pairs. For example, for DNA, the metagenomic fragment reads may have read lengths of less than 100 base pairs, and the metagenomic file 1103 produced therefrom may contain millions of DNA fragment reads.

In the embodiment illustrated in FIG. 11, instrument 1100 receives a metagenomic file 1103 as input. However, in other embodiments, instrument 1100 may also comprise an extractor and sequencer and be capable of receiving a sample as input and producing a metagenomic file 1103 therefrom (see, e.g. FIG. 2). In still other embodiments, the instrument 1100 may receive metagenomic fragment reads individually and produce a metagenomic file 1103 including the received metagenomic fragment reads.

Instrument 1100 may be coupled to a sequencer and receive a metagenomic file 1103 directly from the sequencer, but this is not required. Instrument 1100 may also receive the metagenomic file 1103 indirectly from one or more sequencers that are not coupled to instrument 1100. For example, instrument 1100 may receive a metagenomic file over a communication network from a sequencer, which may be located remotely. Or, a metagenomic file 1103, which has previously been stored on a storage medium, such as a hard disk drive or optical storage medium, may be input into instrument 1100.

In addition, instrument 1100 may receive a metagenomic file 1103 or metagenomic fragments reads in real-time, immediately following sequencing by a sequencer or in parallel with sequencing by a sequencer, but this also not required. Instrument 1100 may also receive a metagenomic file 1103 or metagenomic fragments at a later time. In other words, the characterization of populations of microorganisms in a sample performed by instrument 1100 may be performed in-line with sample collection, metagenomic fragment extraction and metagenomic fragment sequencing, but all of the steps may be handled separately and/or in a stepwise fashion.

Instrument 1100 may operate under the control of a sequencer that sequences the metagenomic fragments extracted from a sample, but no connected processing or even direct communication between 1100 and a sequencer is required. Instead, the characterization of populations of microorganisms in a sample performed by instrument 1100 may be performed separately from sample collection, metagenomic fragment extraction and/or metagenomic fragment sequencing.

Figure 12:
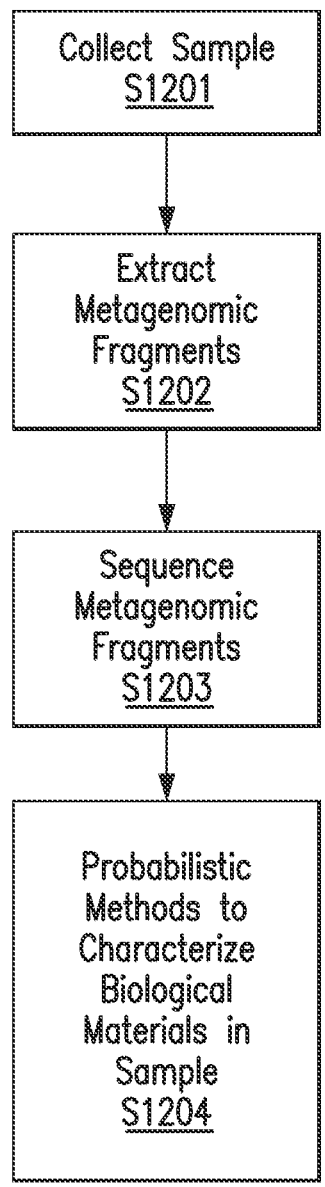
FIG. 12 is top-level flowchart illustrating a process that may be performed to characterize populations of microorganisms in a sample.

FIG. 12 is top-level flowchart illustrating a process that may be performed to characterize populations of microorganisms in a sample. In step S1201, a sample is collected. In step S1202, metagenomic fragments, which may be nucleic acid and/or protein and/or metabolites, are extracted. In step S1203, the metagenomic fragments are sequenced, and metagenomic fragment reads are obtained. In step S1204, a metagenomic analysis process is performed to characterize the identities and relative populations and/or concentrations of organisms contained within the sample based on the metagenomic fragment reads, which may be in the form of a metagenomic file.

As described above, the metagenomic analysis process of step S1204 may be performed in-line with the sample collection, metagenomic fragment extraction and metagenomic fragment sequencing of steps S1201-S1203, but all of the steps may alternatively be handled separately and/or in a stepwise fashion.

In step S1204, the metagenomic analysis process to characterize the biological material in the sample may be run by instrument 1100. The sequenced metagenomic file 1103 of random base pairs of the metagenomic fragment reads may comprise the input for the metagenomic analysis process run by instrument 1100. The characterization may include identifying the species and/or sub-species and/or strains of organisms contained in the sample.

The metagenomic analysis process perform probabilistic methods, which may include probabilistically comparing metagenomic fragment reads to one or more qualified reference genomic databases to characterize the microbial community of the sample. The probabilistic methods may be performed in parallel (i.e., concurrently) with sequencing of the metagenomic fragments, as fast as the metagenomic fragments are sequenced (i.e., real-time sequencing), sequentially following sequencing of the metagenomic fragments, or at any time after sequencing of the metagenomic fragments has been completed.

In some embodiments, the sequencing instrument may continue to collect longer and more strings of sequence information in parallel with the comparison. Subsequent sequence information may also be compared and may increase the confidence of a genome or species identification in the sample. The method does may not need to wait for sequence information assembly of the short reads into larger contigs. However, as noted above, in some embodiments, all of the metagenomic fragment reads used in the metagenomic analysis process of step S1204 may be input as a single metagenomic file.

In some embodiments, the metagenomic analysis process run in step S1204 may characterize the microbial community of the sample by identifying the microbial community of the sample at the species and/or sub-species and/or strain level with their relative concentrations or abundance. In particular, the genomes of organisms contained within the sample may be identified based on the metagenomic fragment reads by performing probabilistic comparisons for each of the plurality of metagenomic fragment reads against genomic sequence information contained in one or more reference genomic databases.

Whereas identification of microorganisms in a metagenomic sample, based on direct sequencing and probabilistic matching, is independent of sequencing method or machine type, the results can be affected by machine error of the sequencer and the effectiveness/efficiency of the extraction of materials to be sequenced. Accordingly, for relative accuracy in determining relative populations of organisms at the sub-species or strain or species level, step S1204 may include normalizing for machine error by using a larger number of statistically significant metagenomic fragment reads. For example, in some embodiments, fragment extension (i.e., moving from fragment reads having a length of n to fragment reads having a length of n+1) and/or the creation of more fragments may be performed to increase accuracy. If strain identification is critical for a treatment decision, then the system and method of the invention may feed back a request for more sequencing.

Figure 13:
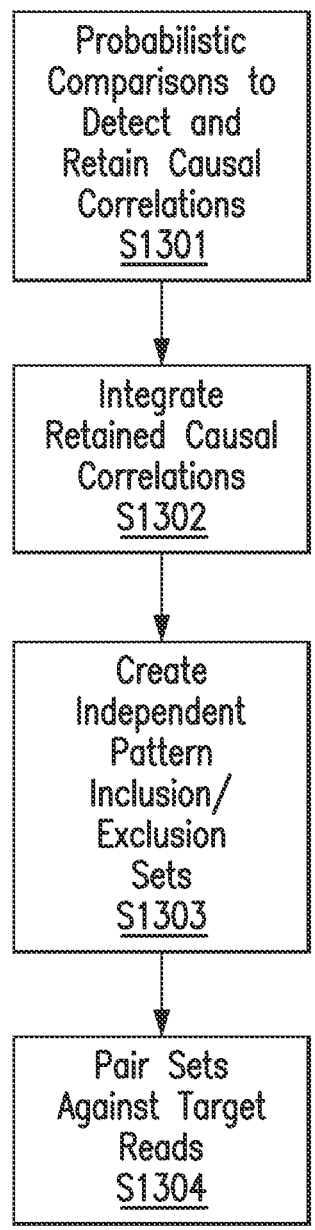
FIG. 13 is a flowchart illustrating a process that may be performed to identify genomes of microorganisms contained within a sample.

FIG. 13 is a flowchart illustrating an exemplary process that may be performed in step S1204 to identify genomes of organisms contained within a sample. The metagenomic fragment reads may be input into the process shown in FIG. 13 in the form of a metagenomic file 1103. In step S1301, instrument 1100 may perform probabilistic comparisons of the metagenomic fragment reads against sequence information (i.e., genome reads) contained in one or more reference genomic databases containing genomic identities of microorganisms. In particular, the probabilistic comparisons may compare each of the plurality of metagenomic fragment reads to genome reads of the one or more reference databases to identify matches between a metagenomic fragment read obtained from the sample and one or more genomes of microorganisms contained in a reference genomic database. The matches may be in the form of causal correlations between a metagenomic fragment read and a genome of the reference genomic database, and, when detected, the causal correlation is retained.

The probabilistic comparisons may include, but are not limited to, perfect matching, subsequence uniqueness, pattern matching, multiple sub-sequence matching within n length, inexact matching, seed and extend, distance measurements and phylogenetic tree mapping. Further, the probabilistic comparisons may use the Bayesian approach, Recursive Bayesian approach or Naïve Bayesian approach, but is not limited to any of these approaches.

The probabilistic comparisons may determine that a causal correlation exists between a metagenomic fragment read and a subsequence in a reference genetic database when the probabilistic comparisons determines that the metagenomic fragment read and the subsequence of the reference genomic database are similar enough to imply a biological relationship. Additionally, the genetic subsequence may have close cousins from related strains or similar biologic function, and, as the reference genomic database is assumed to be incomplete, the probabilistic matching may also consider fragment correlation with close cousins to be causal as well. When comparing millions of metagenomic fragment reads with billions of subsequences, in some embodiments, one only expects about tens of millions of causal fragments among the million billion putative comparisons.

The probabilistic comparisons of step S1301 produces probabilistic results, which in some embodiments may be in the form of a probability map of probabilities that species and/or strains of microorganisms within a reference genomic database are present in the sample. The probability map may enable correlation of the probabilities of the probability map with relative populations and/or concentrations of microorganisms contained within the sample.

In some embodiments, the probability map may have a structure based on statistical counting and correlation process with the structure built on the hierarchy of the correlation process. The structure may be related to the degree of relatedness of target genomes to other genomes present (i.e., if *Shigella* is present, there is a degree of relatedness to nonpathogenic *Escherichia* present in the sample). Relatedness may be tiered by the taxonomy level (e.g., strain, species, genus, etc.). The distance of the relatedness can be represented as color. For example, unique scores (i.e., high probability) would be red, and blue would represent low probability. In turn, for example, this "color map" may be described as a heat map (or probability map) in gradations of probability from red (high) to low (blue).

Further, in some non-limiting embodiments, step S1301 may compensate for machine error by normalizing the probability map using a larger number of statistically significant reads than the number of reads needed for accurate characterization if no machine error were assumed. Statistically, most any signal can be recovered from a noisy environment through the integration of more data. In one embodiment, for sequencing error, suppose that the probability of no errors in an n-long sequence is $(1-p)^n$. If $n=20$ and $p=0.01$, then the probability of no errors in a sequence of 20 base pairs is 82%, while if $n=20$ and $p=0.1$, this probability is 12%. All other things equal, one requires 7 times more data in the second case to make equally strong statements of metagenomic content based on samples of n-long fragments.

The compensation of machine error may be complicated by analysis of the variance of the distributions and nonindependence of related genomics strains. In an artificial example, where A and B are markers of genomes α and β; suppose $P(A|A)=P(B|B)=p$ and $P(A|B)=P(B|A)=1-p$; the probability of observing A given α and the probability of observing B given β are each q; and the metagenomic mixture of the sample is $r\alpha+(1-r)\beta$. Then to first order given T observations, $$\mu(A)=(rqp+(1-r)q(1-p))T=(1-r-p+2rp)qT \sim \text{var}(A)$$
$$\text{sigmage}(A) \sim \text{sqrt}\{(1-r-p-rp)qT\}$$

Thus the significance of the predictions of the probabilistic methods increases exponentially with the square of the number of reads. In some embodiments, precise prediction may utilize an estimate of p (e.g., the sequencing error rate), and the number of metagenomic fragment reads used in metagenomic analysis process may be selected so that sequencing errors will be normalized to near zero.

In one embodiment, in step S1302, instrument 1100 may integrate (i.e., aggregate) the retained causal correlations by, for example, genomic strain to significantly raise the signal-to-noise ratio of causally present strain in the metagenomic population relative to non-causal strains and thereby achieve high species identification of the genomes of microorganisms contained in the sample. In other words, the retained causal correlations for each of the genomic strains of the reference genomic database may be added together.

The method may also include steps to further disambiguate between closely related strains and to detect the presence of multiple, related strains of differing concentrations. In step S1303, instrument 1100 may create independent pattern sets of subset inclusion and subset exclusion from the set of closely related genomes. The independent pattern sets are n-mer patterns that occur in some but not all of the genomes of the closely related genomes. For example, if genomes closely related genomes G1-G3 are included in a reference genomic database, instrument 1100 may create the following independent patterns sets: (1) n-mer patterns A and B, which occur in genome G1 but not genomes G2 and G3; (2) n-mer pattern C, which occurs in genome G2 but not genomes G1 and G3; (3) n-mer patterns D, E, F and G, which occur in genome G3 but not genomes G1 and G2; (4) n-mer pattern H that occurs in genomes G1 and G2 but not genome G3; and (5) n-mer patters G, I and H that occur in genomes G2 and G3 but not genome G1. Note that genome G1 and G3 may have no unique markers, and, as a result, the pattern set of n-mer patterns which occur in genomes G1 and G3 but not in genome G2 is the null set.

In its simplest form, a pattern set may be those n-mers which occur in a genome X but not any other. Assuming there are K such patterns with multiplicity among M total patterns in the genome and a concentration of C, if there are L patterns in the fragment reads, then $L*C*K/M=H$ hits are expected among the K patterns or $C \sim H*M/(K*L)$. In some embodiments, this estimate may be adjusted for sampling error and database accuracy. Simple least squares, hill climbing and linear programming methods may be used with pattern sets that involve multiple genomes and to combine multiple estimators for a given genomic concentration. A pattern set may also be those n-mers which occur in a plurality of genomes (e.g., genomes X, Y and Z) but not any other.

In step S1304, for each independent pattern set, instrument 1100 may pair the set against target reads. For example, in step S1304, for each independent pattern set $\{P\_i\}$, instrument 1100 may compare the patterns within the set against the target fragment reads. If a causal genome (i.e., a genome found in the metagenomic sample) is among the genomes in the set, then all patterns within the set $\{P\_i\}$ should be found in the target fragment reads—subject to potential sampling bias, genomic concentration and strain variation. The extent of coverage of the pattern set $\{P\_i\}$ by the target reads thereby provides a concentration estimate for each genome which was included in the creation of the pattern set. The result of each pairing between an independent pattern set and the target is an independent estimate. Further, the result of each of the pairings is an independent estimate of concentration of the genome in the set that gives a fine-grain estimate of genomic strain concentrations even for closely related microbial communities.

In steps S1301 and S1302, instrument 1100 may perform primary filtering to determine what species and strains from one or more reference databases may be present in the metagenomic sample. Then, in steps S1303 and S1304, instrument 1100 may perform secondary and tertiary filtering to eliminate both false negatives and false positives and to identify at the strain level what is present in the sample.

Although the exemplary process of step S1204 to identify genomes of microorganisms contained within a sample illustrated in FIG. 13 includes steps S1301-S1304, not all of those steps are necessary for the genome identification in accordance with the present invention. In fact, the steps are separable. In some embodiments, steps S1303 and s1304 may be seeded with genomes without resort to steps S1301 and S1302. For example, steps S1303 and s1304 may instead be seeded via a list of *V. Cholerae* strains for a *V. Cholerae* study. Additionally, step S1303 may be performed blind across the entire database as a very large precomputation step even though more dynamic approaches, such as the inclusion of steps 1301 and 1302, which requires less hardware and storage, may also be used.

Also, the steps shown in FIG. 13 are capable of determining changes in biodiversity and capable of detecting engineered pathogens. For example, the method may account for biodiversity by identifying (a) mobile genetic elements through lateral gene transfer, recombination, or plasmid or other mobilome insertion; (b) insertions and deletions; and (c) identification and detection of near cousin strains related by mutation, insertion, deletion.

Figure 14:
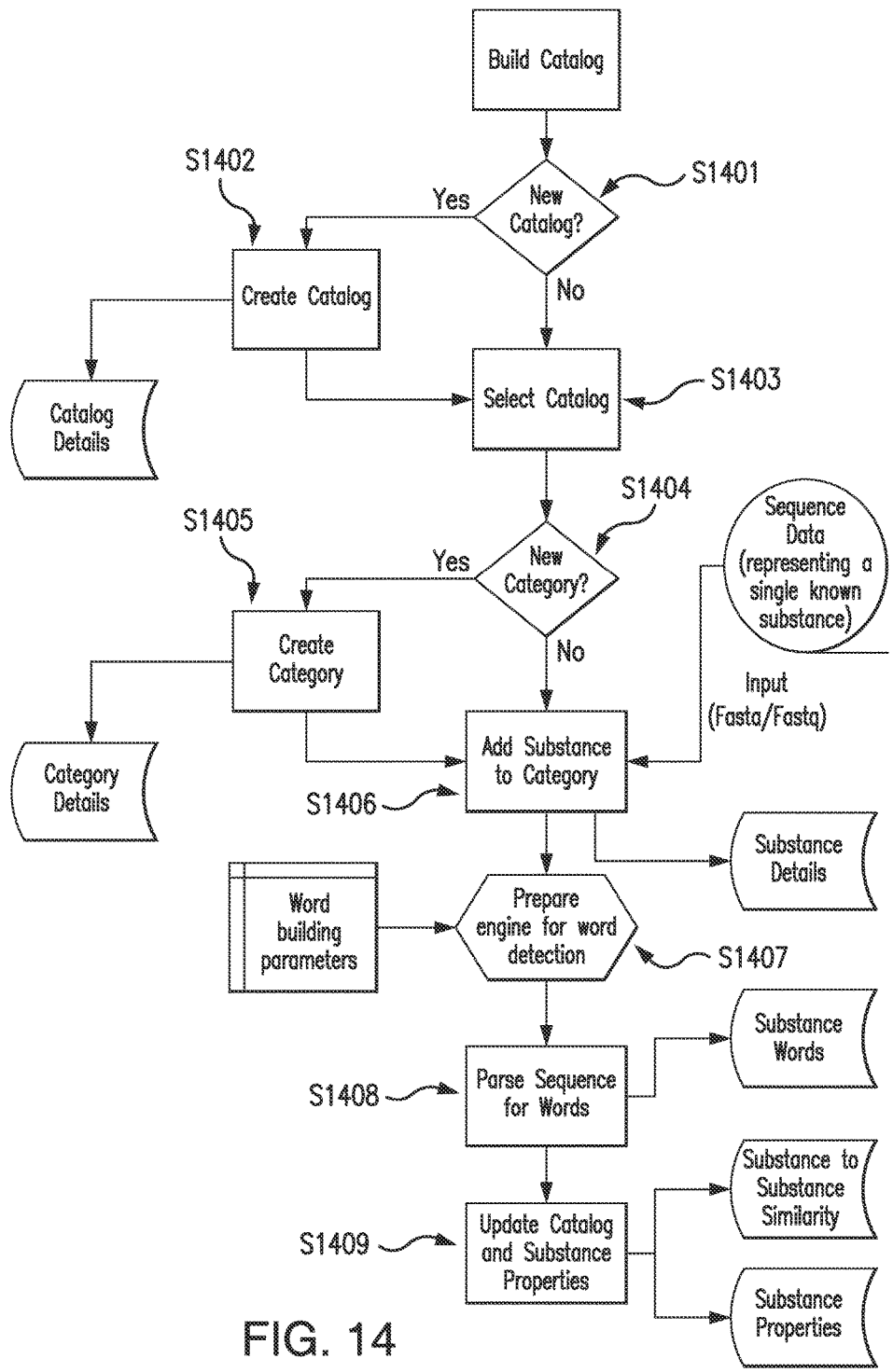
FIG. 14 is a flowchart illustrating an embodiment of a substance cataloging process.
Figure 15:
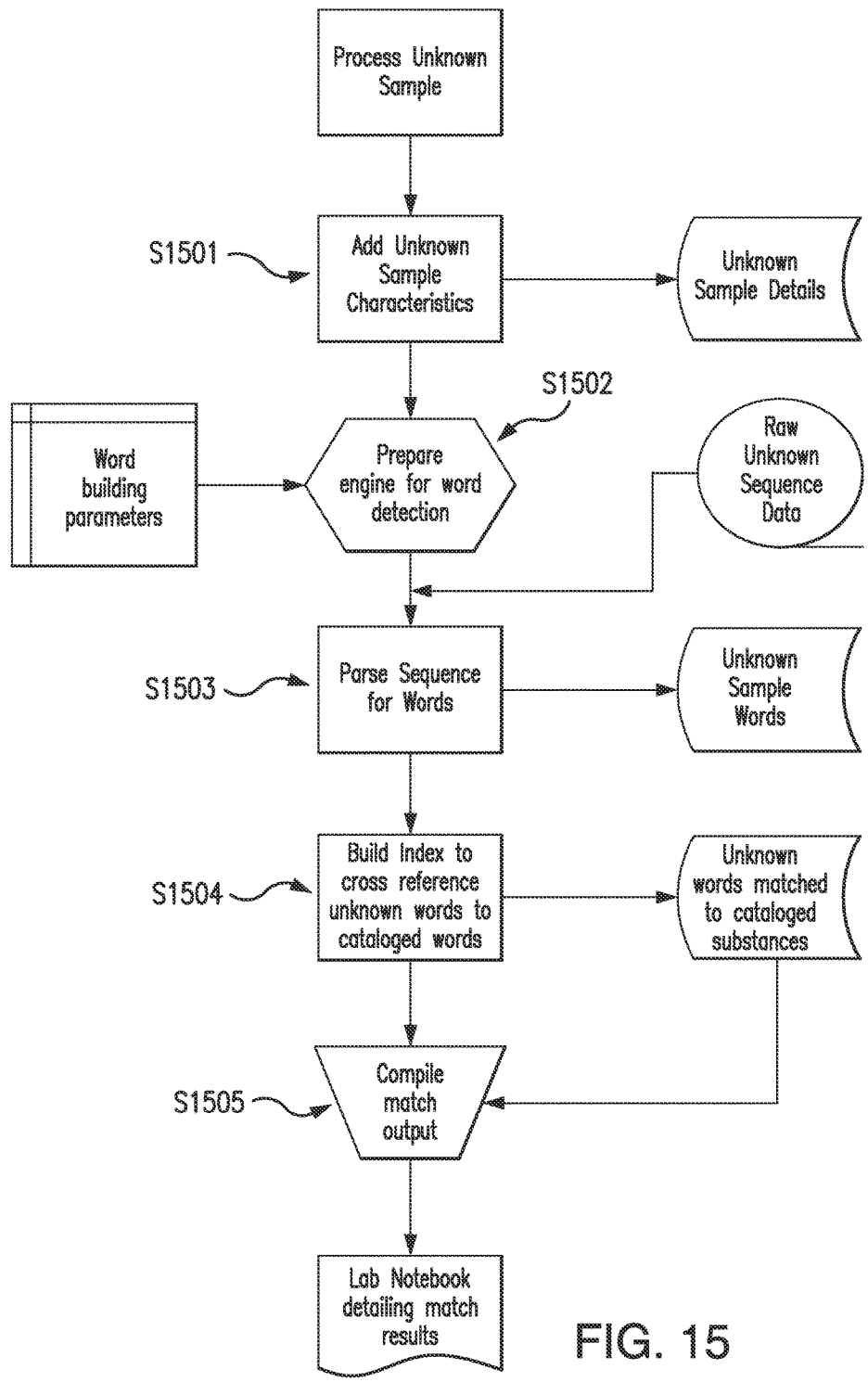
FIG. 15 is a flowchart illustrating an embodiment of an unknown sample parsing and identification process.

Although the probabilistic metagenomic analysis process of step S1204 to characterize the identities and relative populations and/or concentrations of organisms contained within a sample based on metagenomic fragment reads may be performed by many processes, a particular non-limiting embodiment of a probabilistic metagenomic analysis process that may performed by instrument 1100 to carry out step S1204 is described below with references to FIGS. 14-16. The particular non-limiting embodiment is referred to as Comparator Engine.

The Comparator Engine is composed of three main components: (1) the Comparator Engine database, (2) substance cataloging processes, and (3) unknown sample parsing and identification processes. The basic premise behind the Comparator Engine is that the sequence data for a substance can be divided up into words, and that a sub-set of these words can be used to identify the original substance. At a high level, the Comparator Engine takes the known substances, and builds a catalog of words. Then, to analyze samples of unknown contents, the Comparator Engine takes the sequence information from the samples of unknown contents and divides that sequence information into a word list. Next, the Comparator Engine takes the words from the sample and matches them to the words in the catalog. The output of the match is then summarized by counting the number of words that match by known substance.

The Comparator Engine database may be built on a server, such as the Microsoft SQL Server 2005. The cataloging, parsing and word analysis tools may be writing in a programming language, such as Java. The primary user interface may used, such as Java Server Pages running on a Tomcat application server. Further, the entire system may be housed on a single server machine, such as on a single Windows Server machine.

In general, the database design of the Comparator Engine system may be very simple. The simplicity of the database facilitates performance. Accordingly, the data base may be designed to keep overhead associated with the underlying data relationships to a minimum.

The data model may have the following high level data structures: (1) Catalog, (2) Substance, (3) Category, (4) Substance Category, (5) Substance Words, (6) Unknown, and (7) Unknown Words. The data base may be partitioned into logical Catalogs. For example, a Catalog could represent sequence information representing the sequences associated with the 8 pathogens list, or it could be all enteric species. A Substance is a known sequence (e.g., genomic identity) assigned a name. Typically, a Substance may be a sequence associated with an individual species, such as *Vibrio cholerae*, but a Substance can also be a sequence associated with an individual known strain or sub-species. A Category may define a name that can be assigned to one or more Substances for the purpose of grouping. For example, a Category may allow species to be grouped together into a genus. A Substance Category may define the relationship between a Substance and a Category. A Substance may have one or more Categories, and a Category may have one or more Substances. The Substance Words structure may be, essentially, the dictionary of known words. It may contain all the words identified in the sequence data for each Substance. The Unknown structure may be labeled sequence data of unknown contents. This may represent the metagenomic fragment reads obtained from a sample containing genetic material from a plurality of organisms, which may be in the form of a metagenomic input file 1103.

The metagenomic input file 1103 may contain sequence data in a particular format. For example, the 454, Illumina, or any FASTA or FASTQ format may be used. The Unknown Words structure may be words contained in the sequence data of the unknown contents (i.e., a sample containing genetic material from a plurality of organisms).

The substance cataloging process in one embodiment refers to the processing surrounding loading sequenced and aligned sequence files, associated with known species, into the database. An illustrative embodiment of the substance cataloging process is shown in FIG. 14. The inputs into the substance cataloging process may be (1) sequence data representing a single known Substance, (2) a Catalog into which records for the Substance are to be added, and (3) a Category (e.g., genus or species or strain) to which the Substance belongs. The inputs into the substance cataloging process may also include word building parameters, but it is also possible for the word building parameters to be set by default. The sequence data for the Substance may be in the form of an input file, which may have a FASTA or FASTQ format. The sequence data for the Substance may be genome reads obtained from one or more reference genomic databases containing genomic identities of organisms.

In step S1401, the substance cataloging process determines whether the identified Catalog into which records for the Substance are to be added is a new Catalog. If the identified Catalog is a new Catalog, in step S1402, the identified Catalog is created. Step S1402 may output the details of the created Catalog. Then, in step S1403, the created Catalog is selected. Otherwise, if the identified Catalog is not a new Catalog and already exists, the existing Catalog is selected in S1403. In step S1404, the substance cataloging process determines whether the identified Category to which the substance belongs is a new Category. If the identified Category is a new Category, in step S1405, the identified Category is created. Step S1405 may also output the details of the created Category. Then, in step S1406, the created Category is selected. Otherwise, if the identified Category is not a new Category and already exists, the existing Category is selected in S1406.

Step S1406 also adds the Substance to the selected Category by reading the sequence data representing the known Substance and associating it with the selected Catalog. Then, in step S1407, the process initiates the word finding process by preparing for word detection. Step S1407 may read in any word building parameters input to the process. Next, in step S1408, the read sequence data representing the known Substance is parsed for words. In this step, the process splits the sequence into fragments, called words, interrogates the resulting word list or vector, and selects words to add to the Substance Words structure or table or file. The word finding process is described in greater detail below. Step S1408 may output the Substance Words table. Then, in step S1409, the process may update the Catalog by adding the Substance Words table and various comparison reports may be generated. For example, in step S1409, the process may output Substance to Substance similarities and Substance properties reports.

The substance cataloging process may be repeated for a number of Substances, and, in this manner, the data base may be populated with one or more Catalogs each having one or more Categories and one or more Substances. The resulting Catalog(s) of words from known substances may be utilized to identify unknown substances using words generated from the unknown substances.

In other embodiments, the substance cataloging process may also store all of the reference words generated from all of the cataloged known substances (i.e., all words from each of the Substance Words structures generated for each cataloged Substance) in a hash table. Such a hash table populated with all of the reference words may indicate how many of the cataloged substances have each of the references words. Thus, the hash table may report which reference words are unique (i.e., belonging to only one substance) and which reference words are common to more than one known substance. In this way, one or more hash tables may be used to indicate the reference words that are unique to a genus, species, sub-species and/or strain. Knowing whether a word is unique or common may be used in the identification of the unknown substances of the sample.

The unknown sample parsing and identification process refers to the processing surrounding parsing the sequence data of the unknown contents into words and comparing the words of the unknown contents to the words of the known substances to identify the unknown contents. An illustrative embodiment of the unknown sample parsing and identification process is shown in FIG. 15. The sequence data representing the unknown contents is input into the unknown sample parsing and identification process. The sequence data may represent the metagenomic fragment reads obtained from a sample containing genetic material from a plurality of organisms and may be in the form of a metagenomic input file 1103. The metagenomic input file 1103 may contain sequence data in a particular format. For example, the 454, Illumina, or any FASTA or FASTQ format may be used. The inputs may also include word building parameters, but it is also possible for the word building parameters to be set by default.

In step S1501, the sequence file representing the unknown contents from a sample is read in and added to the Comparator Engine database as Unknown. Step S1501 may also output details of the unknown sample. The details of the unknown sample may include the date and time the sample was taken, the geographic location in which the sample was taken, and/or other similar metadata. In step S1502, the process initiates the word finding process by preparing for word detection. Step S1502 may read in any word building parameters input to the process. Next, in step S1503, the read sequence data representing the unknown contents in the Unknown structure is parsed for words. In this step, the process splits the sequence into fragments, called words, interrogates the resulting word list or vector, and selects words to add to the Unknown Words structure or table or file. The word finding process is described in greater detail below. Step S1503 may output the Unknown Words table.

Once the word parsing of step S1503 is complete, in step S1504, the words associated with the Unknown are compared to words in the dictionary of cataloged known substances (i.e., the words in the Substance Words structures of a Catalog). In step S1504, the process builds an index to cross-reference unknown words to cataloged words in the dictionary. Step S1504 may output unknown words that have been matched to words in the dictionary of known substances. The matches may be exact matches and/or inexact (i.e., partial or similar) matches.

In some embodiments, the comparison process of S1504 looks for exact matches on words unique to a single known Substance, as well as total matches to any words in the dictionary. Step S1504 may also compute a weighted relatedness score by assigning a weight factor to the types of matches. For example, exact matches to unique words for a particular Substance would have the highest weight, exact matches to words unique to Category would have a lower weight, exact matches to very common words would have an even lower weight and so on. In this fashion, the comparison process of S1504 may compute a score that considers the relative value of a particular match. In other embodiments, the comparison process of S1504 may perform partial matching using, for example, the Levenshtein approach. Various search techniques that could be utilized include a data base engine SQL based search, a Simple string comparison search, a Regular Expression Search with the ability to look for inexact matches; the Levenshtein Distance approach, a Bayesian Classifier, a Vector Classifier, and/or a Google-Type Search Engine. Some embodiments using the Levenshtein Distance approach may first build a set of matches that are similar, and then use the Levenshtein Distance approach to compute the similarity score.

In step S1505, the process compiles the matches between words of the unknown sample and words of the cataloged known substances. For example, step S1505 may calculate a rank for the known substances that helps separate strains that show up because of similarity to a better match from those that are actually present in the unknown contents of the sample. The rank may, for example, be based on, for each known substance, the sum of the total number of matches between the words of the unknown sample and the words of the known substance, a sum of the number of distinct matches, the total number of unique words, and/or number of distinct unique matches. Step S1505 may also produce and output the compiled matches and/or closely related words in an output spreadsheet.

The Comparator Engine may also perform a comparative analysis between two or more items to compute the relatedness between two or more sequences. The sequences can be between strains of known substance or between unknown samples. The comparative analysis compares word lists and the overlapping count is reported. The comparative analysis may compute a relative relatedness score based on how many words are available in each set and how many matched. For example, the relatedness of assemblies of words may be tied back to the strains (words) in the reference database to produce relative identities. The uniqueness value of the word may be used for probability, and the biological significance of the word may be included. Words shared between organisms may have a lower score, and the degree of sharing across the number of different strains may be considered in the score.

Figure 16:
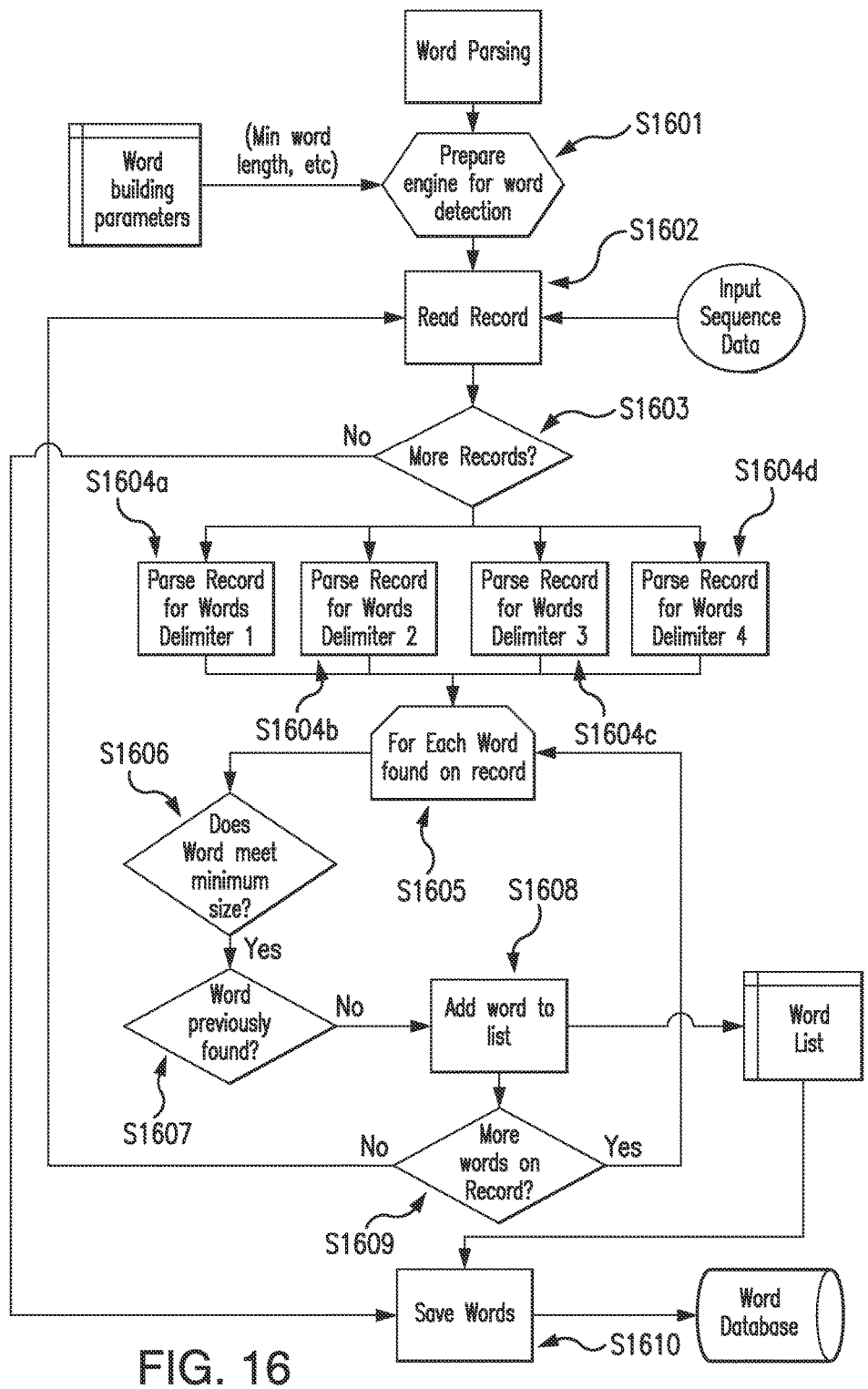
FIG. 16 is a flowchart illustrating an embodiment of a word finding process.

An illustrative embodiment of the word finding process, which may be used in the substance cataloging process and/or the unknown sample parsing process, is shown in FIG. 16. The word finding process may begin in step S1601 by preparing for word detection. Step S1601 corresponds to step S1407 of the substance cataloging process shown in FIG. 14 and to step S1502 of the unknown sample parsing process shown in FIG. 15. Step S1601 may read in any word building parameters input to the process. In this embodiment, the word building parameters may include a minimum word length. The word finding process may also set the minimum word length to a default minimum word length, which may be, for example, 19 letters.

Next, in step S1602, the word finding process reads sequence data, which may represent a known substance or an unknown sample. In step S1603, the process determines whether there are any more records (i.e., sequence data) in need of processing. If there are more records, the process proceeds to step S1604, where the sequence data is parsed for words. In step S1604, the process may make, for example, four passes, S1604$a$ through S1604$d$, through the sequence data. In each of passes S1604$a$ through S1604$d$, a different one of the sequence letters is used as a boundary character. For example, pass S1604$a$ may use "A" as a boundary character, pass S1604$b$ may use "C" as a boundary character, pass S1604$c$ may use "T" as a boundary character, and pass S1604$d$ may use "G" as a boundary character. In passes S1604$a$ through S1604$d$, the word finding process may split the sequence into fragments, called words, at the word boundary character.

In step S1605, each of the words generated in passes S1604$a$ through S1604$d$ of parsing step S1604 is selected for additional processing. For instance, in step S1606, the process determines whether each word has a length equal to or greater than the minimum word length, which may be set according to the input word building parameters or by default. If step S1606 determines that a word meets the minimum size requirement, step S1607 may determine whether the word was previously found. If steps S1606 and S1607 determine that a word has a length equal to or greater than the minimum word length and has not previously been found, the word is added to a word list in step S1608. In step S1609, the process determines whether there are more words that have not been processed. If there are more words, the process repeats steps S1605 through S1609 until all the words generated by passes S1604$a$ through S1604$d$ have been processed. Once all the words have been processed, and step S1609 determines that there are no more words, the process returns to step S1602, where any additional sequence data is read.

If step S1603 determines that there are no more records (i.e., sequence data) in need of processing, the process proceeds to step S1510, where the word list is saved to the Comparator Engine database. If the word finding process is run by the substance cataloging process, the saved word list may be used as the Substance Words file or table. If the word finding process is run by the unknown sample parsing process, the saved word list may be used as the as the Unknown Words file or table.

In some embodiments, the minimum word length used by the word finding process is greater than or equal to 18 letters and less than or equal to 27 letters. In some embodiments, the minimum word length used by the word finding process is greater than or equal to 19 letters and less than or equal to 25 letters. In a particular embodiment, the minimum word length used by the word finding process is 19 letters.

In some embodiments, the sequence data of the unknown content input to the problem will be a large collection (e.g., 10^9) of short sequences of k letters, k-mers, from the environmental sample, and the output will be the organisms that may be in the environmental sample. While some k-mers are shared between multiple organisms, those that are unique to a species, sub-species and/or strain of organism, or to their genus, will be the most valuable.

The number of k-mers from the sample that may come from an unknown substance (e.g., a dangerous target) in order to identify that substance and whether it is likely that the target can be identified with a single k-mer may be considered in selecting the length at which to set the minimum word length. As noted above, the k-mers may be compared in a hash-table of all the k-mers occurring in all cataloged known substances, which could, for example, be all bacterial sequences in a reference genomic database, such as GenBank.

In some non-limiting embodiments, experimental data suggests that a word length k equal to 19 letters (i.e., k=19) is effective as a minimum word length. In a non-limiting example, a sample of 30 complete sequences of different strains of bacteria from GenBank was analyzed. Roughly 5% of 17-mers were shared between multiple organisms. However, for organisms with no common relative in the sample, the species could be uniquely identified by over 99% of the 19-mers in their genome. For example, 99.4% of all 19-mers were unique to *Chlamydia trachomatis* (1.1 Mb) and 99.9% were unique to *Synechocystis* (3.5 Mb). Slightly longer lengths, such as 25 letters, may also work well. However, in this non-limiting example, lengths of much longer lengths did not work as well because minor differences between similar strains may have prevented matches. Hence, in a non-limiting embodiment, only one 19-mer is needed to identify the bacteria in the great majority of cases, and the hash table could report how many bacteria have the 19-mer, in the rare cases where it is not in a unique strain.

In this non-limiting example, of these 30 bacteria, there were two pairs of closely related organisms: *E. coli* W3110 and *E. coli* K-12 and *Helicobacter pylori* 26695 and *Helicobacter pylori* J99. In both of these cases, the genomes of related organisms were nearly the same length (4.5 Mb for *E. coli* and 1.7 Mb for *H. pylori*). The diversity between these pairs was quite varied. The two *H. pylori* sequences shared only 40% of its 19-mers with the other, while the two *E. coli* strains were virtually identical.

The preliminary results of this non-limiting example indicate that there is substantial ability to determine at least the genus of bacteria in an environmental sample and in many cases the species with only one 19-mer. When multiple 19-mers are used, the improved detection results in a greatly improved chance of accurate detection of at the species, sub-species or strain level. Even for extreme cases such as *E. coli* where 99.9% of the 19-mers are shared between members, multiple 19-mers will greatly improve detection of which *E. coli* strain the 19-mers are from. For example, if 1000 distinct 19-mers are drawn from a sample with only one of the two *E. coli* species, there is a 63% chance (1−1/e) that at least one of them will be unique to the *E. coli* species. By comparison, for two *H. pylori* sequences, five 19-mers will allow the specification of a single choice with probability 99%.

In one embodiment, when 19 letters are used as the minimum word length, the substance cataloging process builds a Catalog of 19-mers (i.e., words having a minimum length of 19 letters) for each known genome (e.g., substance). Words are built from 19-mers of 3 nt (nucleotide) combinations. Using the embodiment of the word finding process shown in FIG. 16, four passes are made, for example, across each genome to account for breaking the sequence string by each of the four nucleotides (e.g., A, C, T and G). The fourth nt may be the toggle basepair tag for the word. This creates breaks in the sequence for comparison. This limits the size of the data for matching and increases the speed of comparisons between the catalogs of reference genome dictionaries and the sample sequence file parsed into words. In some embodiments, duplications of words are not counted. In some embodiments, a word is scored when there is perfect match between a sample sequence file word and a reference word. The probability of correct scoring is one of four possibilities: a) correct target, b) closely related genome, c) accidental hit, d) lateral transferred sequence between genomes.

The relative concentrations of the organisms in the sample may be determined by, for example, comparing the number of matches for each of the cataloged known substances. In some embodiments, the relative concentrations may additionally, or alternatively, be determined by considering the frequency that a matching word occurs.

In the identification of genomes of microorganisms contained within a sample based on metagenomic fragment reads using the probabilistic metagenomic analysis processes described above, the number of read lengths deployed for identifying relative populations depends on the relative abundance and concentration of the microorganisms of the sample, the size of the microbial genome, depth of coverage and sequence accuracy. Sequence accuracy is affected by multiple factors that may include, for example, sample preparation, sequence context, sequencing chemistry, base calling software and the machine error of the sequencing method deployed to produce the metagenomic file (i.e., instrument accuracy).

In one embodiment, for machine error of less than 1%, for a genome containing 5 million base pairs, the system and method of the present invention may be capable of (i) accurately identifying strains having a concentration of 0.001 or greater using a metagenomic file containing as few as one thousand short metagenomic fragment reads from a metagenomic sample, and (ii) performing species identification using a metagenomic file containing as few as approximately one hundred short metagenomic fragment reads. Accordingly, the system and method of the present invention is capable of performing strain level identification for 0.1% detection level using a metagenomic file containing as few as approximately one million total metagenomic fragment reads of the metagenomic sample. Moreover, as few as ten thousand reads may give species level granularity to 1% detection levels. However, it is noted that the fidelity of the reference genomic database may be a source of error. If a strain of a microorganism present in the sample is not present in the reference database, identification of the strain may not be possible. Also, if the strain of microorganism present in the sample is in the reference database, then the number of strains for the species of microorganism may affect error level. The number of strains and their relative concentrations found within the target also may affect error level.

For a machine error of less than 10%, with all else being equal, the system and method of the present invention may be capable of performing (a) species identification using a metagenomic file containing as few as several hundred metagenomic fragment reads, and (b) strain level identification with concentration estimates using a metagenomic file containing as few as tens of thousands of metagenomic fragment reads. However, in some embodiments, depending on length, a metagenomic file containing hundreds of thousands or millions of metagenomic fragments may be used to increase strain identification and concentration estimate reliability.

In certain embodiments, the estimated accuracy of the system and method of the present invention for identification at the species level may be greater than 98%. The estimated accuracy of the system and method of the present invention for identification at the strain level may be greater than 92% provided that the reference genomic database contains the strain. In an extreme example, when there are several very closely related strains differing by less than 100 base pairs in 1 million (e.g., related strains of *B. anthracis*), near neighbor accuracy of the identification may be very high. Plus, further iterations with additional algorithmic tools may be used to identify the precise strain at greater than 92% accuracy. For example, probabilistic methods may utilize built-in specific signatures of the closely related strains.

No other methods and systems are currently available to provide similar levels of accuracy.

In one non-limiting example, the system and methods of the present invention were used to identify pathogens in metagenomic samples from patients admitted to a hospital to be treated for diarrheal disease. The causality of disease was identified in every case by DNA direct sequencing of the metagenomic sample followed by the genome identification according to an embodiment of the present invention using probabilistic matching.

The results of the genome identification through probabilistic matching were compared blinded with orthogonal methods from 26 standard bioassays which demonstrated 100% accuracy. Table 1 below shows the results of the comparison for 9 samples taken from the patients admitted for treatment of diarrheal disease. Some pathogens, such as *Helicobacter pylori* or community of pathogens, which were characterized by the genome identification of the present invention but were not detected by the battery of conventional methods constituting a pool of 26 bioassays based on predetermined bacterial, viral and parasitic targets. In addition, relative to the direct sequencing and genome identification of the present invention, the conventional methods are extensively labor and time intensive. For example, conventional methods include classical serotyping, culture, molecular, microscopic and immunoassays and require substantially greater time compared with metagenomic sequencing and population identification of the present invention. Even for the samples where probable etiologies were identified, the conventional analysis does not provide a definable and efficient treatment modality. By contrast, the breadth and depth of direct DNA sequencing and full sample profiling along the etiology achieved by the present invention demonstrate the dominant causal agent and in many cases causal agents which are a community of pathogens rather than single pathogen. This finding of polymicrobial infection reiterates the importance of dynamic diagnostic methods and their advantages over the concurrent static methods being used for disease diagnosis.

TABLE 1

Etiology of diarrheal disease samples as identified by conventional methods vs. the direct sequencing and identification of the present invention

| Sample No. | Etiology as identified by a battery of 26 bioassays | Etiology as determined by direct sequencing in combination with bioinformatic identification for rapid medical diagnosis |
|---|---|---|
| 1 | *V. parahaemolyticus* | *Vibrio parahaemolyticus* |
|  |  | *Shigella dysenteriae* Sd 197 |
|  |  | *Shigella boydii* CDC 3083-94 |
|  |  | *Escherichia coli* HS |
|  |  | *Eubacterium eligens* ATCC 27750 |
|  |  | *Veillonella parvula* DSM 2008 |
|  |  | *Leuconostoc citreum* KM20 |
|  |  | *Bacteroides vulgatus* ATCC 8482 |
|  |  | *Citrobacter rodentium* ICC168 |
|  |  | *Eubacterium rectale* ATCC 33656 |
| 2 | *V. parahaemolyticus* | *Vibrio parahaemolyticus* |
|  |  | *Escherichia coli* SMS-3-5 |
|  |  | *Shigella boydii* CDC 3083-94 |
|  |  | *Leuconostoc citreum* KM20 |
|  |  | *Eubacterium eligens* ATCC 27750 |
|  |  | *Bacteroides vulgatus* ATCC 8482 |
|  |  | *Klebsiella pneumoniae* MGH 78578 |
|  |  | *Veillonella parvula* DSM 2008 |
| 3 | *Shigellae* | *Shigella sonnei* Ss046 |
|  |  | *Shigella flexneri* 2a 2457T |
|  |  | *Escherichia coli* 55989 |
|  |  | *Klebsiella pneumoniae* MGH 78578 |
|  |  | *Citrobacter rodentium* |
| 4 | *Shigellae* | *Shigella sonnei* Ss046 |
|  |  | *Escherichia coli* B REL606 |
|  |  | *Escherichia coli* K 12 substr W3110 |
|  |  | *Bacteroides vulgatus* ATCC 8482 |
|  |  | *Escherichia coli* ATCC 8739 |
|  |  | *Klebsiella pneumoniae* MGH 78578 |
|  |  | *Eubacterium rectale* ATCC 33656 |
|  |  | *Eubacterium eligens* ATCC 27750 |
|  |  | *Parabacteroides distasonis* 8503 |
| 5 | *Vibrio cholerae* O1 & *Shigellae* | *Vibrio cholerae* O1 |
|  |  | *Shigella sonnei* Ss046 |
|  |  | *Escherichia coli* 55989 |
|  |  | *Escherichia coli* B str. REL606 |
|  |  | *Shigella flexneri* 2a str. 2457T |
|  |  | *Escherichia coli* DH1 |
| 6 | No pathogen identified | *Bacteroides fragilis* YCH46 |
|  |  | *Escherichia coli* DH1 |
|  |  | *Klebsiella pneumoniae* MGH 78578 |
|  |  | *Streptococcus pyogenes* MGAS2096 |
|  |  | *Bacteroides vulgatus* ATCC 8482 |
|  |  | *Eubacterium rectale* ATCC 33656 |
|  |  | *Parabacteroides distasonis* ATCC 8503 |
|  |  | *Bacteroides thetaiotaomicron* VPI-5482 |
| 7 | No pathogen identified | *Klebsiella pneumoniae* MGH 78578 |
|  |  | *Shigella boydii* CDC 3083 94 |
|  |  | *Escherichia coli* SE11 |
|  |  | *Escherichia coli* BL21 DE3 |
|  |  | *Eubacterium rectale* ATCC 33656 |
|  |  | *Clostridium novyi* NT |
|  |  | *Cytophaga hutchinsonii* ATCC 3340 |
|  |  | *Mycoplasma pulmonis* UAB CTIP |
|  |  | *Psychromonas ingrahamii* 37 |
| 8 | No pathogen identified | *Bacteroides fragilis* YCH46 |
|  |  | *Klebsiella pneumoniae* MGH 78578 |
|  |  | *Escherichia coli* UMN026 |

TABLE 1-continued

Etiology of diarrheal disease samples as identified by conventional methods vs. the direct sequencing and identification of the present invention

| Sample No. | Etiology as identified by a battery of 26 bioassays | Etiology as determined by direct sequencing in combination with bioinformatic identification for rapid medical diagnosis |
|---|---|---|
| 9 | No pathogen identified | Eubacterium rectale ATCC 33656<br>Eubacterium eligens ATCC 27750<br>Bacteroides thetaiotaomicron VPI-5482<br>Bacteroides vulgatus ATCC 8482<br>Parabacteroides distasonis ATCC 8503<br>Veillonella parvula DSM 2008<br>Citrobacter rodentium ICC168<br>Helicobacter pylori G27<br>Escherichia coli SMS-3-5<br>Escherichia coli UMN026<br>Candidatus Sulcia muelleri SMDSEM<br>Buchnera aphidicola str. Cc |

From a separate analysis of diarrheal samples (mostly cholera) from patients experiencing more severe diarrhea, the characterization of the microorganisms by the present invention enabled the conclusion that, for these patients, there was a mixture of pathogens (e.g., *Vibrio cholerae* and *Giardia lamblia*), and the severity of the disease presented were most likely not caused by a sole pathogen (e.g., *Vibrio cholerae*), rather a mixture of pathogens acting in a synergistic manner. This sort of synergistic etiology enabled by the characterization performed by the present invention, where one pathogen attributes the disease causality and others elevate disease severity, is capable of providing invaluable information in disease management and control which is beyond the scope of any existing diagnostic technology.

One of the standard methods for identifying bacteria is by using the robustness of 16S rDNA for taxonomic placement. The 16S population assessment targets the 16S-23S rRNA gene intergenic transcribed spacer (ITS) region. However, 16S rDNA is limited to genus level resolution. In other words, 16S rDNA identifies bacteria only to the genus, family and order level. Each genus, family and order constitutes a large number of species representing both commensals and pathogens. Plus, 16S rDNA is only specific typically at the family-level and may even underperform for genus level identification.

Figure 17A:
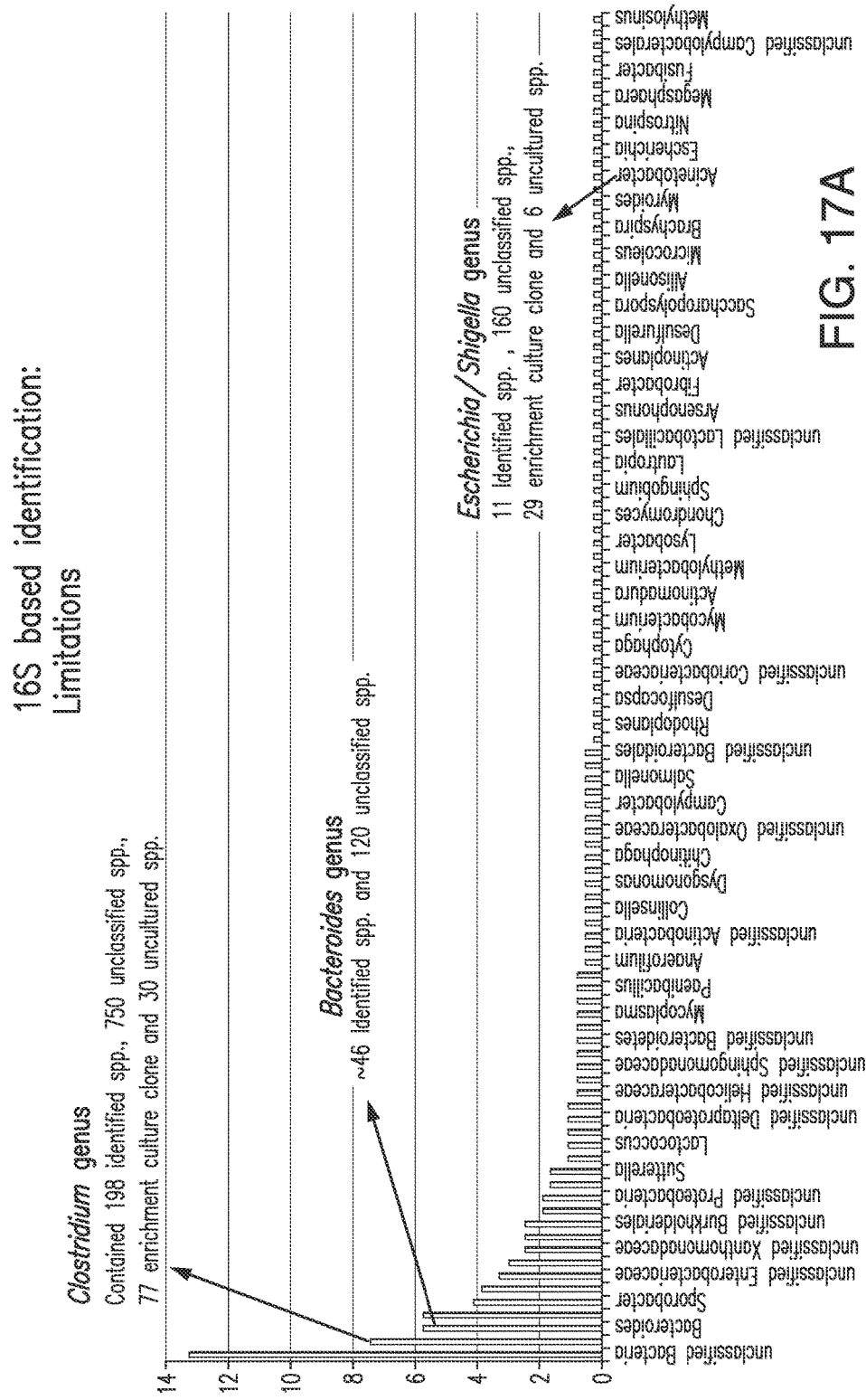
Figure 17C:
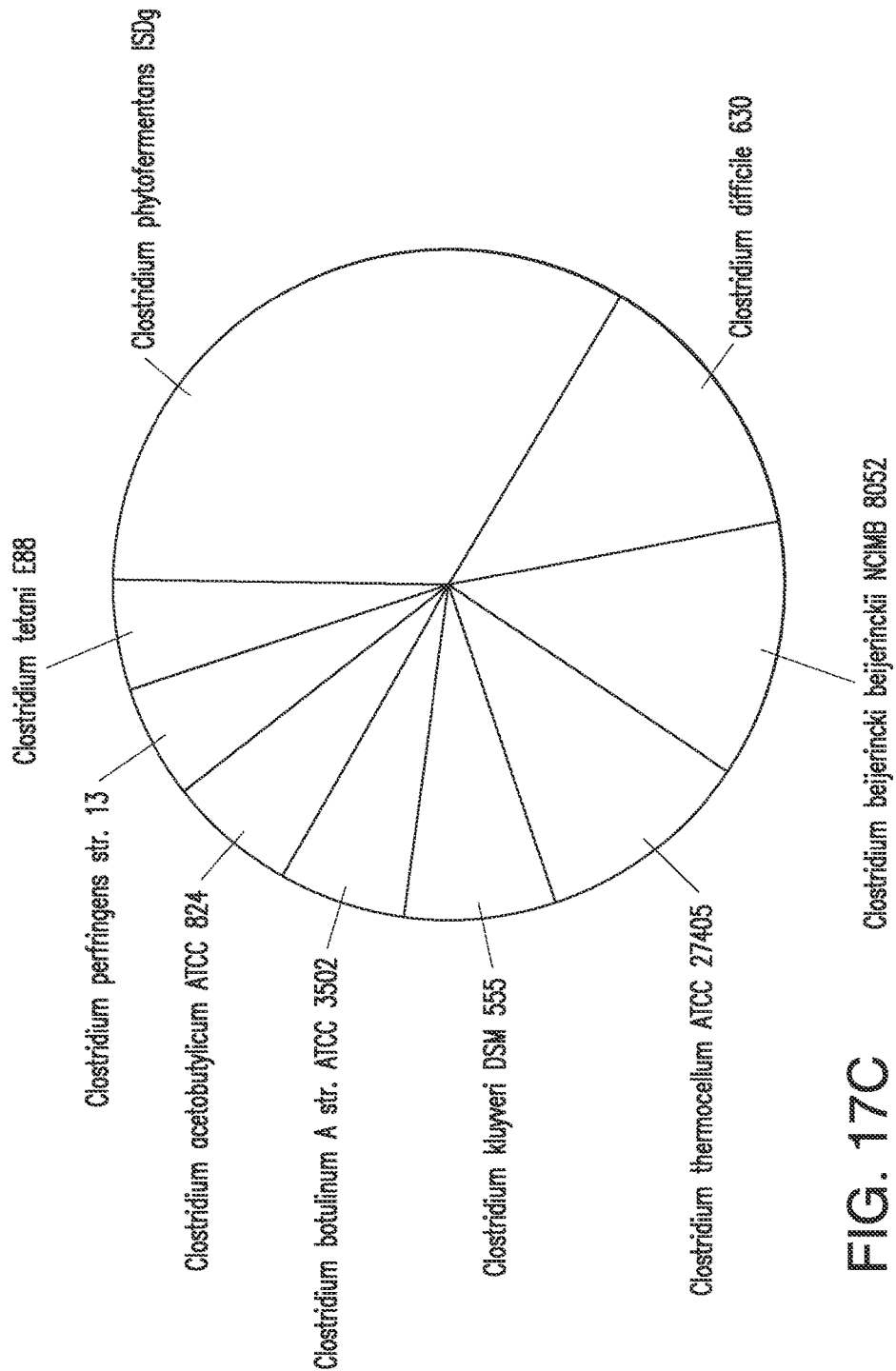
Figure 17D:
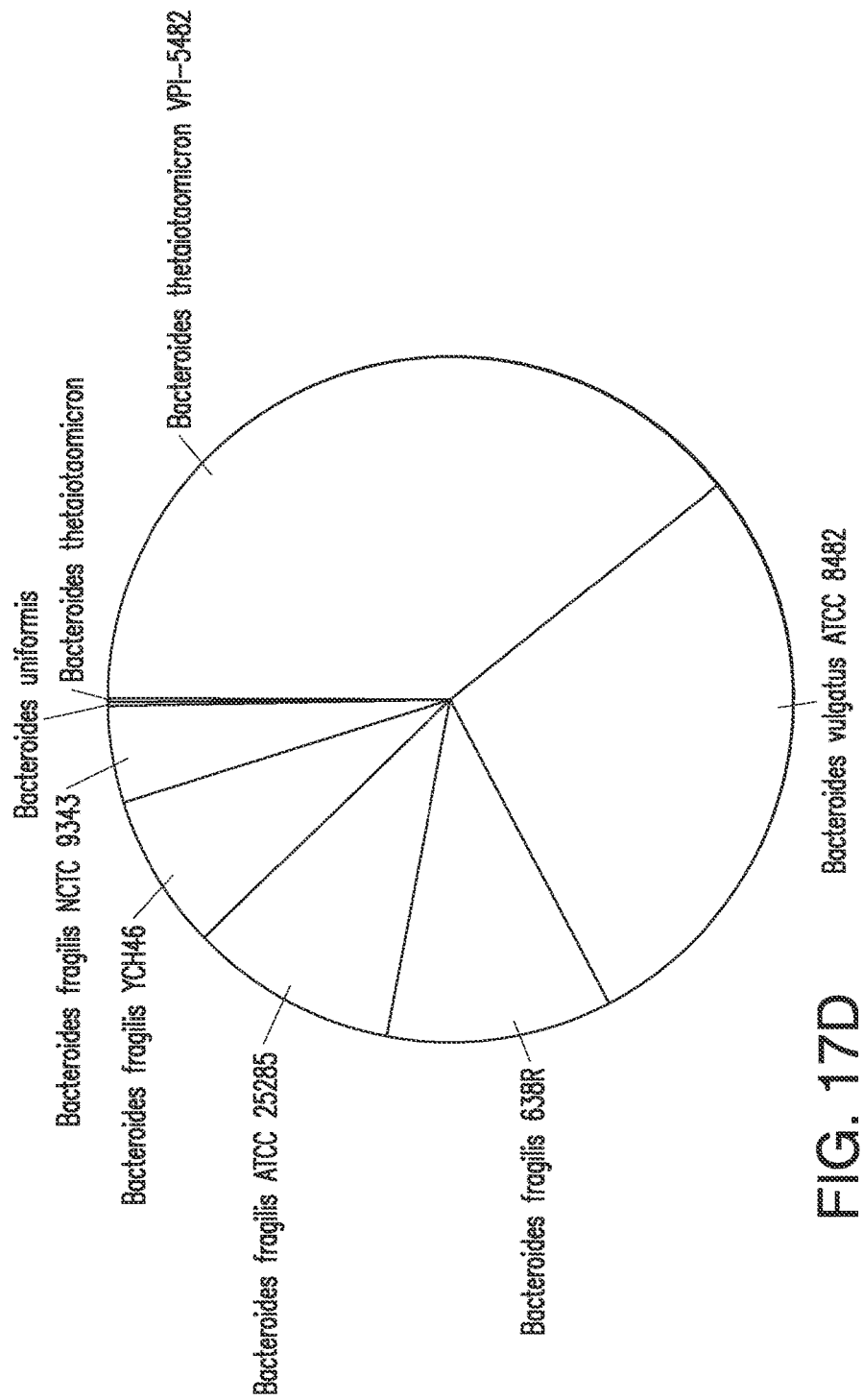
Figure 17E:
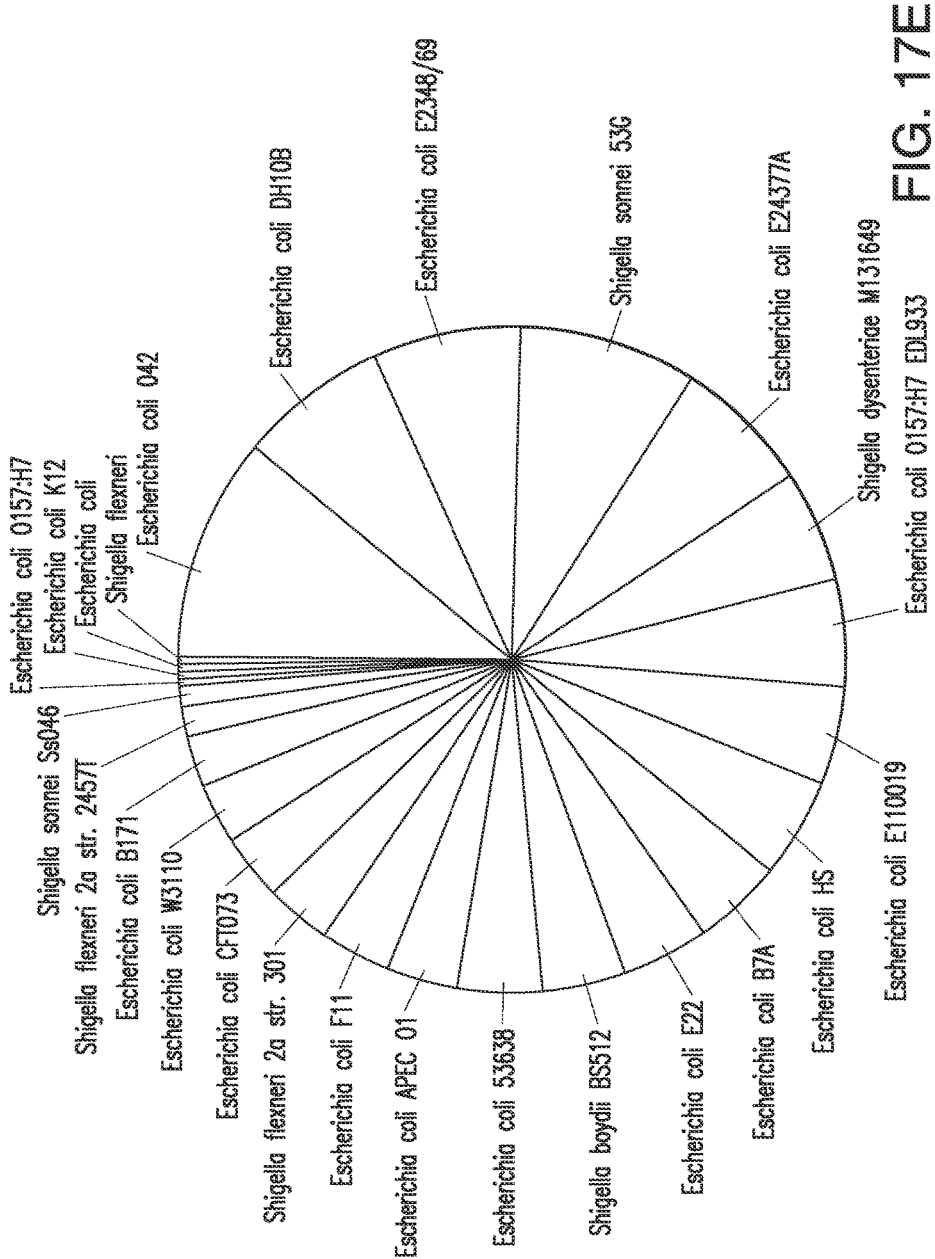

FIGS. 17A-17E illustrate the relative population measurements of 16S rDNA compared to the direct DNA sequencing with genomic identification of the present invention. FIG. 17A shows population measurements using 16S rDNA, and FIGS. 17B-17E show populations measurements using the direct DNA sequencing with genomic identification of the present invention. FIGS. 17C-17E show species and strains of the *Clostridium* genus, *Bacteroides* genus, and *Escherichia/Shigella* genus, respectively, identified by the direct DNA sequencing with genomic identification of the present invention, along with their relative concentrations.

As shown in FIGS. 17A-17E, the direct DNA sequencing with metagenomic identification of the present invention further classified each genus identified by 16S to the species and/or strain levels. For example, the *Clostridium* genus includes commensal species but also includes four main species responsible for disease in humans: *Clostridium diffcile, Clostridium botulinum, Clostridium perfringens* and *Clostridium tetani*. While 16S identified that the sample contained bacteria of the *Clostridium* genus, as shown in FIG. 17C, the direct DNA sequencing with metagenomic identification of the present invention identified *Clostridium phyiofermentans* ISDg, *Clostridium diffcile* 630, *Clostridium beijerincki beijerincki* NCIMB 8052, *Clostridium thermocellum* ATCC 27405, *Clostridium kluyveri* DSM 555, *Clostridium botulinum* A str. ATCC 3502, *Clostridium acetobutylicum* ATCC 824, *Clostridium perfringens* str. 13 and *Clostridium tetani* E88. Further, the direct DNA sequencing with metagenomic identification of the present invention additionally identified the concentrations of the identified *Clostridium* species/strains relative to each and relative to other microorganisms of the sample.

In regard to *Bacteroides*, *Bacteroides* are normally mutualistic, and only few species (e.g., *B. fragilis*) are opportunistic human pathogens. Similar to the results with the *Clostridium* genus, while 16S identified that the sample contained bacteria of the *Bacteroides* genus, as shown in FIG. 17D, the direct DNA sequencing with genomic identification of the present invention identified *Bacteroides thetaiotaomicron* VPI-5482, *Bacteroides vulgates* ATCC 8482, *Bacteroides fragiles* 638R, *Bacteroides fragiles* ATCC 25285, *Bacteroides fragiles* YCH46, *Bacteroides fragiles* NCTC 9343, *Bacteroides uniformis* and *Bacteroides thetaiomicron*. Here again, the direct DNA sequencing with metagenomic identification of the present invention additionally identified the concentrations of the identified *Bacteroides* species/strains relative to each and relative to other microorganisms of the sample.

The relative concentrations in FIGS. 17B-17E were based on the number of observed "hits" for a particular set of read lengths belonging to a specific microorganism. The lower the number of hits, the lower the relative concentration. Accuracy at low relative concentrations is based on probability scores determined by comparing read length to genomic database(s). Given an estimate of the system processing error, the percentage of hits observed from a given set of expected patterns yields a concentration estimate with error bars. The present invention may employ multiple, independent sets which enable improved metagenomic disambiguation to be obtained, namely detection and identification of species and strains.

Figure 18:
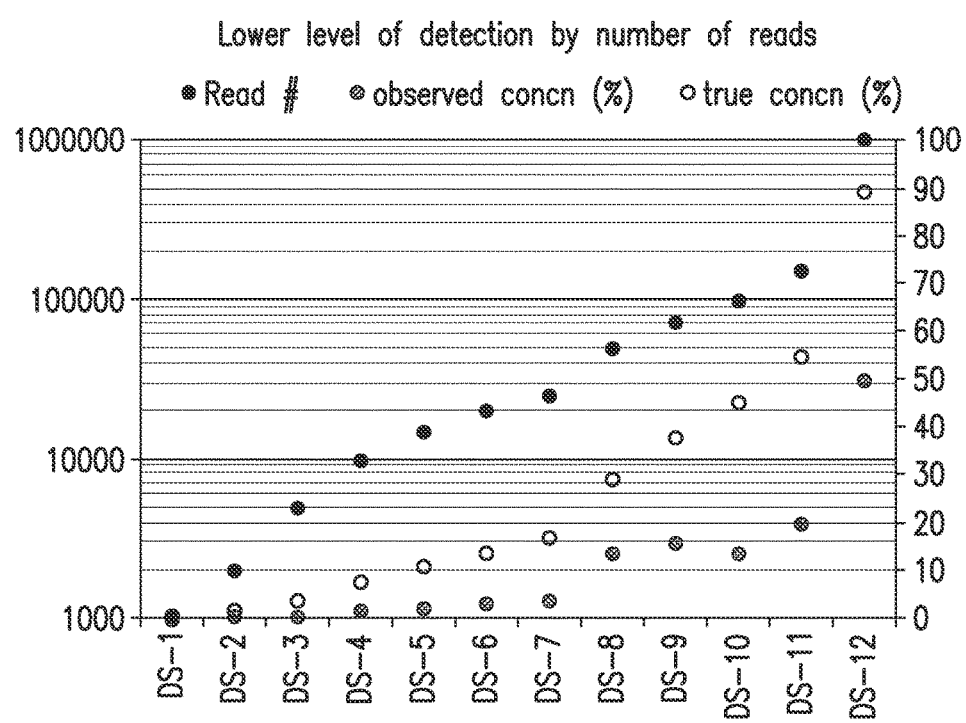
FIG. 18 illustrates a comparison of relative observed concentration and actual concentration in a sample with relative number of reads.

FIG. 18 compares relative observed concentration and actual concentration in a sample with relative number of reads. A serial dilution of one genome was used to create a sample set of different concentrations. Dilution Series (DS) 1-12 represent concentrations of 0.8%, 1.6%, 4%, 7.5%, 11%, 14%, 17%, 29%, 38%, 45%, 55% and 89%, respectively. The results shown in FIG. 18 also demonstrate that the system and methods of the present invention can precisely identify a microbial species with its relative concentration from a complex metagenomic mixture even if it is represented by only 1000 short (~72 bp) reads, and, the observed relative concentrations are in good agreement with the actual concentrations even when the target species are present at very low concentration.

The largest sources of error for determining sensitivity, relative concentrations, and lower levels of abundance are the completeness of the reference database(s) and the degree of closeness between the causal strain and its nearest cousin. For example, if there are only a hundred site differences between two strains, then statistical discrimination between these putative strains is unlikely. The next largest source of error in concentration estimation occurs when two related strains are present in differing concentration levels. System read errors from the strain in greater concentration can bleed into the disambiguation set of the lesser strain artificially raising the estimated concentration of the secondary strain. In some embodiments, the amount of sample DNA required to analyze populations of microorganisms is estimated to be less than or equal to approximately 0.4 ng DNA.

Figure 19:
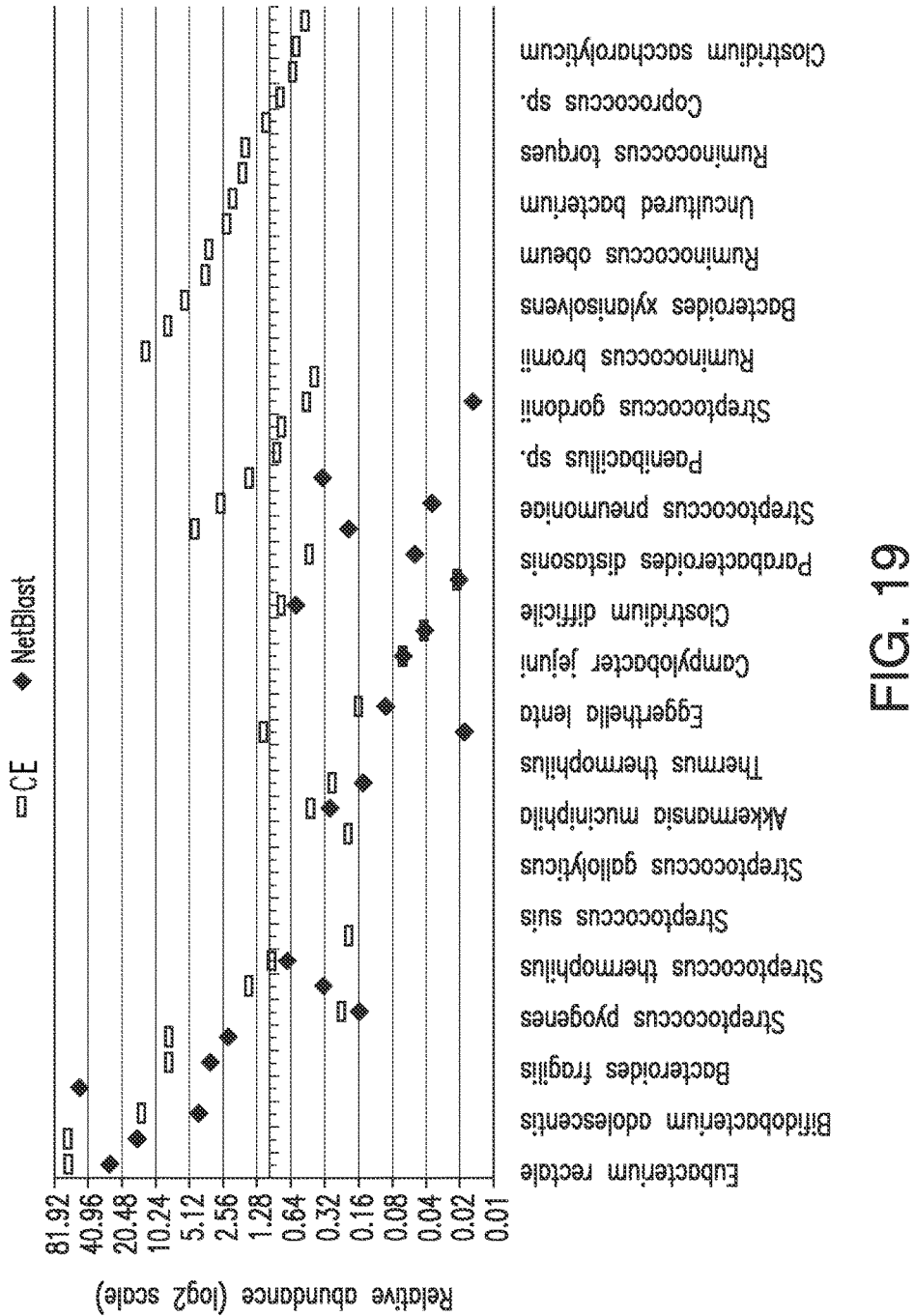
FIG. 19 illustrates an example of the system and method of the present invention applied to measuring populations of the microbiome at the species level for a patient with Crohn's Disease.

Another non-limiting example of the system and method of the present invention applied to measuring populations of the microbiome at the species level is shown FIG. 19 for a patient with Crohn's Disease. FIG. 19 shows a comparison of the results of the Comparator Engine ("CE") to BLAST results and demonstrates that direct DNA metagenomic sequencing and probabilistic matching in accordance with the present invention was able to characterize, with higher precision, populations of bacteria compared with the known BLAST method.

Advantages of a system and method of direct DNA sequencing and metagenomic analysis utilizing probabilistic matching according to the present invention may include, but are not limited to, the following:

(i) the system and method are capable of identifying whole populations of microorganisms in a single sample;

(ii) the system and method are universal and general for all microorganisms whether bacteria, viruses, parasites, fungi, or DNA fragments, plasmids, mobile elements or other;

(iii) the system and method are capable of detecting and identifying simultaneously all types of microorganisms present by employing reference genomic databases;

(iv) the accuracy and sensitivity of the system and method exceeds all conventional methods;

(v) the system and method do not require DNA amplification, and direct extraction and sequencing minimizes errors that might otherwise result from amplification;

(vi) the system and method are independent of sequencing technology and normalizes the machine error of sequencers;

(vii) the system and method account for genetic mutation, including insertions and deletions, pathogenicity islands, insertion of plasmids and mobile genomes or other;

(viii) the system and method are capable of tracing the origin of specific populations of microorganisms including detection of disease agents in food and water;

(ix) the system and method are capable of determining changes in biodiversity and capable of detecting engineered pathogens; and (x) the system and method may have an estimated sensitivity in identifying a single organism in a population of microorganisms of 11n 20 billion.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

For example, although examples focusing on nucleic acid have been provided above, those of skill in the art would understand that the systems and methods of the present invention could be applied to other substances having a sequence nature, such as amino acid sequences in a protein.

What is claimed is:

1. A computer-implemented method of identifying a microorganism in a sample, the method comprising:
   creating a reference word database comprising billions of reference words, wherein the reference word database is generated by an in silica process comprising:
   (i) fragmenting at least first nucleic acid sequences derived from a first reference genome of a first known microorganism and at least second nucleic acid sequences derived from a second reference genome of a second known microorganism into reference words, wherein at least some of the reference words comprise a nucleic acid sequence greater than or equal to 18 letters and less than or equal to 27 letters, and each reference word is associated with a species, sub-species or strain of a known microorganism from which each reference word was derived;
   (ii) cataloging the reference words into a plurality of lists of reference words, wherein the plurality of lists of reference words comprise a first list of reference words associated with the first known microorganism and a second list of reference words associated with the second known microorganism, and
   (iii) storing the plurality of lists of reference words organized as a phylogenetic tree in the reference word database;
   storing the reference word database in a taxonomy cache that includes the Plurality of list of reference words;
   creating a plurality of sample sequence words by an in silica process comprising fragmenting a mixture of nucleic acid sequences derived from a plurality of genomes each corresponding to an unidentified microorganism in a sample into sample sequence words, wherein at least some of the sample sequence words comprise a nucleic acid sequence greater than or equal to 18 letters and less than or equal to 27 letters that corresponds to an unidentified microorganism in the sample;
   comparing the sample sequence words to the reference words in the reference word database;
   filtering out at least a portion of the reference word database in the taxonomy cache to eliminate non-matching portions of the phylogenetic tree based on the comparison, thereby reducing a decision space in the taxonomy cache for identifying one or more microorganisms in the sample, the filtered reference word database including the first list of reference words and the second list of reference words;
   determining a first number of matches between the first list of reference words associated with the first known microorganism and the sample sequence words;
   determining a second number of matches between the second list of reference words associated with the second known microorganism and the sample sequence words;
   determining that the species, sub-species or strain of the first known microorganism is present in the sample based on the first number of matches; and
   determining that the species, sub-species or strain of the second known microorganism is present in the sample based on the second number of matches.

2. The method of claim 1, wherein determining that the species, sub-species or strain of the first known microorganism comprises determining the strain of the first known microorganism.

3. The method of claim 1, wherein comparing the sample sequence words to the reference words in the reference word database comprises the use of probabilistic methods.

4. The method of claim 3, wherein the probabilistic methods comprise correlating probabilities of probabilistic results to relative populations at the species and/or sub-species and/or strain levels.

5. The method of claim 4, wherein the probabilistic results are in the form of a probability map of probabilities that a species and/or sub species and/or strain of a known microorganism is present within the sample.

6. The method of claim 5, wherein the probabilities of the probability map relate to relative populations and/or concentrations of microorganisms contained within the sample.

7. The method of claim 3, further comprising disambiguating between closely related strains in a sample using probabilistic methods comprising:
   creating independent pattern sets of subset inclusion and subset exclusion from reference words associated with a set of closely related strains of the first known microorganism; and
   comparing each independent pattern set to the one or more sample sequence words that match the one or more reference words in the first list of reference words, thereby identifying the at least one of the at least one unidentified microorganism as a strain of the first known microorganism in response to comparing each independent pattern set to the one or more sample sequence words that match the one or more reference words in the first list of reference words.

8. The method of claim 7, wherein an independent estimate of concentration of a genome of the strain of a first known microorganism in the sample is determined in response to comparing each independent pattern set to the one or more sample sequence words that match the one or more reference words in the first list of reference words.

9. The method of claim 3, wherein the probabilistic methods comprise probabilistic matching.

10. The method of claim 6, wherein the probabilistic methods comprise:
    primary filtering; and
    secondary and tertiary filtering to eliminate both false negatives and false positives.

11. The method of claim 1, wherein the comparison accounts for biodiversity.

12. The method of claim 11, wherein accounting for biodiversity comprises identifying: (a) mobile genetic elements through lateral gene transfer, recombination or plasmid or other mobilome insertion; (b) insertions and deletions; and (c) identification and detection of near cousin strains or genes related by mutation, insertion, and/or deletion.

13. The method of claim 1, further comprising:
    detecting and retaining causal correlations between the sample sequence words and the reference words of the reference word database; and
    integrating the retained causal correlations by species or strain to identify a set of microorganisms contained in the sample.

14. The method of claim 1, the method further comprising:
    determining a total number of matches between the reference words and the sample sequence words;
    determining a first relative abundance of the first microorganism based on the first number of matches and the total number of matches; and
    determining a second relative abundance of the second microorganism based on the second number of matches and the total number of matches.

* * * * *